(12) United States Patent
Thelin et al.

(10) Patent No.: US 12,728,076 B2
(45) Date of Patent: Sep. 8, 2026

(54) PACIFIER

(71) Applicant: VIVOLAB AB, Falun (SE)

(72) Inventors: Lars Thelin, Falun (SE); Fredrik Bokvist, Svardsjo (SE)

(73) Assignee: URSATEC GMBH, Tholey (DE)

( * ) Notice: Subject to any disclaimer, the term of this patent is extended or adjusted under 35 U.S.C. 154(b) by 758 days.

(21) Appl. No.: 18/001,794

(22) PCT Filed: Jun. 14, 2021

(86) PCT No.: PCT/SE2021/050575
§ 371 (c)(1),
(2) Date: Dec. 14, 2022

(87) PCT Pub. No.: WO2021/256976
PCT Pub. Date: Dec. 23, 2021

(65) Prior Publication Data

US 2023/0233417 A1 Jul. 27, 2023

(30) Foreign Application Priority Data

Jun. 15, 2020 (SE) .................................... 2050718-2

(51) Int. Cl.
*A61J 17/00* (2006.01)
*A61M 11/00* (2006.01)

(52) U.S. Cl.
CPC ............. *A61J 17/001* (2015.05); *A61J 17/10* (2020.05); *A61M 11/003* (2014.02); *A61M 11/007* (2014.02)

(58) Field of Classification Search
CPC ...... A61J 17/001; A61J 17/00; A61J 17/0053; A61J 17/101; A61J 17/10
See application file for complete search history.

(56) References Cited

U.S. PATENT DOCUMENTS 5,086,765 A * 2/1992 Levine .................. A61M 15/00 128/911
5,261,601 A 11/1993 Ross et al.
(Continued)

FOREIGN PATENT DOCUMENTS

CH 714684 A2 8/2019
CN 1054916 A 10/1991
(Continued)

OTHER PUBLICATIONS

European Office Action dated May 7, 2024 issued in correspoonding European Appln. No. 21734556.0.
(Continued)

*Primary Examiner* — Majid Jamialahmadi
(74) *Attorney, Agent, or Firm* — Harness, Dickey & Pierce, P.L.C.

(57) ABSTRACT

A pacifier comprising a suction part and a housing part, wherein said suction part comprises a nipple and a shield connected to each other, wherein said suction part comprises a passageway through which a fluid can pass from outside a mouth of a user of the pacifier to inside the mouth of the user of the pacifier, and wherein said housing part comprises a housing, wherein said housing is prefilled with a drug which can pass through the passageway into the mouth of the user when the housing part is connected to said suction part and wherein said drug is a drug to be inhaled through the passageway of the suction part.

18 Claims, 19 Drawing Sheets

(56) References Cited

U.S. PATENT DOCUMENTS

| | | | | |
|---|---|---|---|---|
| 5,685,291 | A | 11/1997 | Marsh | |
| 6,110,193 | A | 8/2000 | Chen | |
| 7,418,962 | B1 | 9/2008 | Rao | |
| 2003/0034031 | A1 | 2/2003 | Lev et al. | |
| 2006/0213503 | A1 | 9/2006 | Borgschulte et al. | |
| 2007/0021782 | A1 | 1/2007 | Inoue et al. | |
| 2007/0021783 | A1 | 1/2007 | Viana et al. | |
| 2008/0196716 | A1 | 8/2008 | Wachter | |
| 2009/0062855 | A1* | 3/2009 | Lemery | A61M 16/06 128/200.14 |
| 2010/0044460 | A1 | 2/2010 | Sauzade | |
| 2014/0311483 | A1 | 10/2014 | Engelbreth et al. | |
| 2016/0199609 | A1 | 7/2016 | Gulka et al. | |
| 2018/0221247 | A1 | 8/2018 | Gasperino et al. | |
| 2019/0298618 | A1 | 10/2019 | Becker | |

FOREIGN PATENT DOCUMENTS

| | | | |
|---|---|---|---|
| CN | 1791374 | A | 6/2006 |
| CN | 209450959 | U | 10/2019 |
| DE | 9421156 | U1 | 8/1995 |
| DE | 102017100042 | A1 | 7/2018 |
| DE | 202017006939 | | 11/2018 |
| EP | 0681824 | A1 | 11/1995 |
| EP | 1009362 | A1 | 6/2000 |
| EP | 1625843 | A1 | 2/2006 |
| EP | 3565622 | A1 | 11/2019 |
| GB | 2231497 | A | 11/1990 |
| GB | 2309966 | A | 8/1997 |
| GB | 2327223 | A | 1/1999 |
| GB | 2401795 | A | 11/2004 |
| GB | 2508020 | A | 5/2014 |
| IT | PV20070011 | A1 | 12/2008 |
| KR | 10-1128968 | B1 | 3/2012 |
| NZ | 539381 | A | 7/2007 |
| WO | WO-2008/042951 | A2 | 4/2008 |
| WO | WO-2008/042951 | A3 | 7/2008 |
| WO | 2013/132056 | A1 | 9/2013 |
| WO | 2018/127464 | A1 | 7/2018 |

OTHER PUBLICATIONS

Swedish Search Report dated Jan. 21, 2021 issued in corresponding Swedish Appln. No. 2050718-2.

Swedish Search Report, dated Jun. 29, 2023, issued in corresponding Swedish Patent Application No. 2251382-4.

Chinese Office Action dated Mar. 5, 2025 issued in corresponding Chinese Patent Appln. No. 202180055604.4.

International Search Report for International Application No. PCT/SE2021/050575 dated Jun. 14, 2021.

Office Action issued Jan. 27, 2026 in Korean Application No. 10-2023-7001507.

Examination report issued Feb. 16, 2026 in Indian Application No. 202217071872.

* cited by examiner 541
123
501a
505a
510
121
551
551a
551b
125
503

541
123
505a
543
113
510
553
111b 541
121
543
125
119b 119a
117a
111a
503
109
117
107
117b 541
505b
510
501b
551
551a
551b
503

541
543
113
510
553
111b
505b 541
543
119b

503

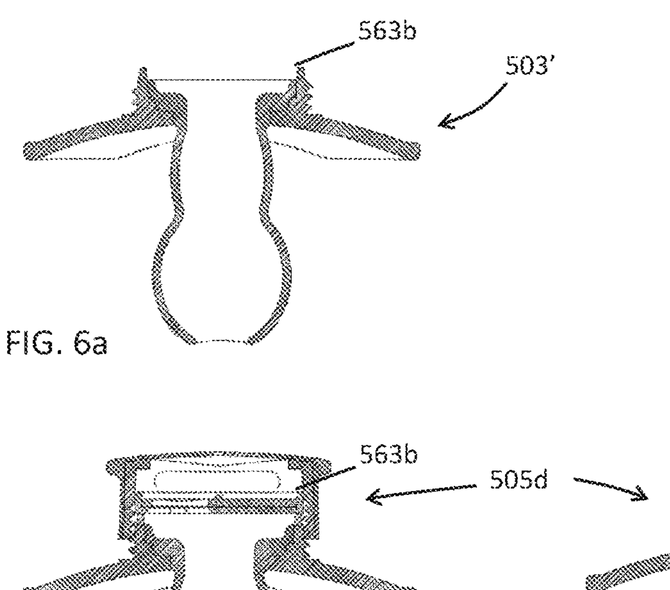
FIG. 6a
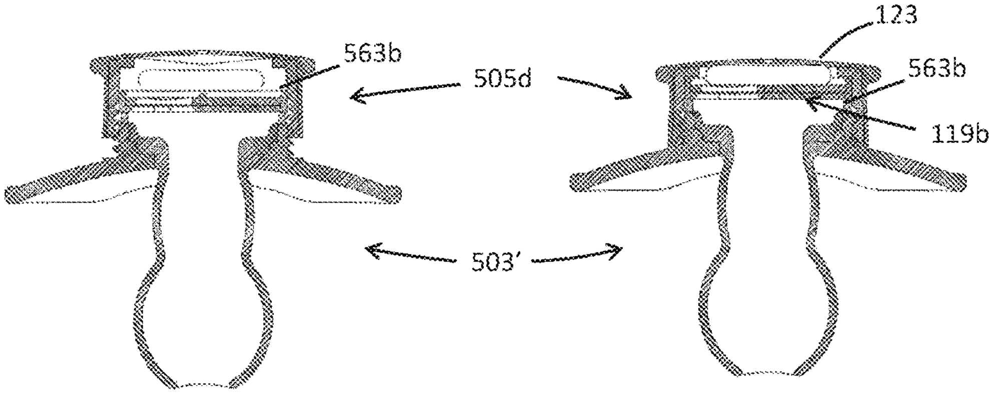
FIG. 6b
FIG. 6c 505f
571b
510'
556
553b'
553a'
503

501f
573
541
571b
543
571b
113
111b
505f
541
543
541'
510'

503

505g
541
561
543
510'
113
111b 501g
541
505g
510'
561
556
551'
553b'
553a'
562'

503

PACIFIER

TECHNICAL FIELD

The present invention relates to a pacifier, an exchangeable housing part configured to be used in a pacifier and to a pacifier system.

BACKGROUND

Feeding of drugs to children can often be problematic. The difficulties of providing inhalation drugs to small children are well known and a field of research of its own. The most effective interface for providing adequate doses of inhaled drugs to children is in the form of a mouthpiece. This allows for the least leakage of drugs. Unfortunately, this type of device is not well accepted by most small children. Other means of providing inhalation drugs to children is the face mask, with or without a spacer. This interface is not widely accepted by children and is prone to leakage. In DE9421156 a pacifier for dispensing inhalants and aerosols is disclosed.

There is still a need for more user friendly devices for feeding of inhalation drugs to small children.

Furthermore, air pollution is a problem. For many years, clean air was regarded as an unlimited resource. However, increasing global air pollution, has directed our attention to technologies related to the improvement of the air we breathe. In its simplest form, individuals in heavily polluted cities have become accustomed to avoiding being outdoors during certain hours of the day or periods of the year, or to wearing breathing masks similar to what is worn in hospitals to avoid infections to spread. In humans, the nose receives and expels air for respiration alongside the mouth. Hair inside the nostrils will filter incoming air, as a first line of defence against dust particles, smoke, and other potential obstructions that would otherwise inhibit respiration, and as a kind of filter against airborne illness. In addition to acting as a filter, mucus contributes moisture to integral components of the respiratory system. The nasal area also heats the incoming air to optimal levels for the body. Thus, by acting as the first interface between the external environment and the delicate lungs, a human nose will condition incoming air, both as a function of thermal and moist regulation and filtration during respiration.

The mouth, on the other hand, is incapable of defending the lungs—breathing through the mouth will expose the lungs to polluted and/or infected air and will also expose the lungs to dry, cold air which can have detrimental effects, especially in small children.

EP 1 009 362 (Hadasit Medical Research) relates to a device that will enable its user to bypass any obstruction in the nasal airways and maintain an open channel to the ambient air. More specifically, this is achieved by providing a pacifier comprising: a nipple consisting of a nipple head and a nipple neck, a shield fixedly attached to, or integral with, said nipple neck, said nipple head being provided with at least one first opening adapted to communicate with the free atmosphere. Further, the pacifier is a breathe-through pacifier having an ambient air open channel between said at least one first opening and the atmosphere so that a user of the pacifier is able to inhale exclusively through the at least one first opening, sufficiently for breathing, whereby any obstruction in the nasal airways is bypassed. It is possible to provide the nipple with a one-way valve sensitive enough to respond to a minimal respiratory effort, but not permitting exhaled air to enter the nipple, thereby preventing the deposition therein of mucous substances. In this case, exhaled air will simply escape between the baby's lips and shield of the pacifier.

US2003034031 (Sleep Up Ltd.) describes a pacifier which facilitates mouth breathing. The pacifier is constructed such that sucking causes an air flow valve to assume a first operational state in which a channel of fluid communication is closed and cessation of sucking allows said air flow valve to assume a second operational state in which said channel of fluid communication is open.

Despite the available technology, there is still a need in the area of pacifiers for improved devices, which are easy to use, not too costly to produce and which are capable of delivering drugs and possibly also improving and conditioning inhaled air in multiple ways.

SUMMARY

An object of the present invention is to provide an improved device for inhalation of drugs.

A further object of the present invention is to provide an improved pacifier for delivering of drugs.

A further object of the present invention is to provide a pacifier system which is capable of both delivering drugs and improving and conditioning inhaled air.

A further object of the present invention is to provide a more versatile and user friendly pacifier.

This is achieved by a pacifier, an exchangeable housing part and a pacifier system according to the independent claims.

According to one aspect of the invention a pacifier comprising a suction part and a housing part is provided, wherein said suction part comprises a nipple and a shield connected to each other, wherein said suction part comprises a passageway through which a fluid can pass from outside a mouth of a user of the pacifier to inside the mouth of the user of the pacifier, and wherein said housing part comprises a housing, wherein said housing is prefilled with a drug which can pass through the passageway into the mouth of the user when the housing part is connected to said suction part and wherein said drug is a drug to be inhaled through the passageway of the suction part.

With the pacifier according to the invention inhalation of a drug can be easily performed also to very small children and without any complicated equipment. The user's own breathing through the pacifier can be used for the administering of the inhalation drug. The pacifier interface is naturally sought after by the child which facilitates the usage and the pacifier furthermore is designed as a mouthpiece device with its drug delivery benefits. Also the timing of inhaling the drug is of great importance and can be a significant challenge, especially in non-cooperative patients such as small children. The time required to inhale the drug and the coordination with inhalation is two components which said invention is optimized for. Since the pacifier is comforting for the child the time for inhalation is virtually unlimited, as opposed to other contraptions such as the face mask which may not be tolerated a long time.

According to another aspect of the invention an exchangeable housing part configured to be used in a pacifier as defined above is provided, wherein said housing part comprises a housing and at least one second connection device which is releasably connectable to at least one first connection device provided in the suction part, wherein said housing is prefilled with a drug which can pass through the passageway into the mouth of the user when the housing part is connected to said suction part and wherein said drug is a drug to be inhaled through the passageway of the suction part.

According to another aspect of the invention a pacifier system comprising a reusable suction part and at least two exchangeable housing parts is provided.

In some embodiments of the invention the suction part is a reusable part and the housing part is an exchangeable part, wherein said reusable suction part and said exchangeable housing part are releasable connectable to each other, wherein said suction part comprises at least one first connection device and wherein said housing part comprises at least one second connection device which is releasably connectable to the at least one first connection device.

Hereby a versatile pacifier is achieved. The suction part can be reused and connected to different housing parts. Hereby for example housing parts comprising different types of drugs or different doses of the drug can be attached to and used together with the same suction part.

In some embodiments of the invention said housing comprises at least one air inlet, whereby air can be drawn into the housing through said air inlet by a user of the pacifier when the user is inhaling through the passageway of the suction part. Hereby the child can breathe normally also during inhalation of the drug. In some embodiments of the invention an air flow from inhalation can also be utilized for preparing the drug into a form suitable for inhalation and for transferring the drug to the user.

In some embodiments of the invention said housing comprises at least one air inlet which is provided with at least one valve such that passage of air via said at least one air inlet only is admitted into and not out from said housing. Hereby there is no risk that drug will pass out via the air inlet.

In some embodiments of the invention said housing part comprises a drug preparation device configured for transferring the drug to the suction part in a form for inhalation.

In some embodiments of the invention said drug is a powder drug for inhalation and said drug preparation device comprises a turbulence device and a dosing device.

In some embodiments of the invention said drug is a liquid drug for inhalation and said drug preparation device comprises an aerosolization device.

In some embodiments of the invention said aerosolization device comprises at least one aerosolization membrane which is a fine pore membrane and/or an oscillating membrane, whereby said liquid drug will be aerosolized when forced through said at least one aerosolization membrane.

In some embodiments of the invention said aerosolization device comprises an oscillating membrane, wherein said oscillating membrane is configured for starting to oscillate when a user of the pacifier inhales whereby the liquid drug will be aerosolized by said oscillations and whereby said oscillating membrane comprises pores which are of a size such that aerosolized drug can pass through the oscillating membrane and further through the housing part to a fine pore membrane or to the passageway of the suction part.

In some embodiments of the invention said housing part further comprises a piercing member arranged for piercing a drug capsule in which said drug is provided when said housing part is provided in a certain position in relation to the suction part hereby allowing the drug to be released from said drug capsule at a certain moment.

In some embodiments of the invention said drug is provided in more than one drug capsule and wherein said housing part can be provided in more than one different positions in relation to the suction part whereby said piercing member will be piercing one drug capsule in each of said positions.

In some embodiments of the invention the drug is provided inside a drug capsule having a breakable capsule cover whereby the drug capsule has a size such that the drug capsule will be compressed and broken when the suction part and the housing part are connected.

In some embodiments of the invention said passageway comprises a first end and a second end between which a fluid can pass, which first end is provided at a first connection interface of the suction part configured for mating with a second connection interface of the housing part and which second end of the passageway is provided in a part of the nipple which is configured to be positioned within a user's mouth during use of the pacifier, whereby a fluid can pass through the passageway between the first connection interface of the suction part and the inside of a user's mouth during use of the pacifier.

In some embodiments of the invention the housing of the housing part comprises an interior space which is defined by a lid, surrounding walls and a second connection interface which is provided opposite the lid, wherein said second connection interface is configured for mating with the first connection interface of the suction part.

In some embodiments of the invention the housing part or the suction part comprises at least one protruding part which will push the second connection interface towards the lid when the housing part and the suction part are connected whereby a pressure will be provided to the interior space, in which the drug initially is provided. Said pressure can both be used for breaking a drug capsule and for transferring the drug through the pacifier, possibly through an aerosolization device.

In some embodiments of the invention a lid of the housing comprises at least one air inlet through which air can pass and wherein the drug is provided within an interior space of the housing such that air passing between the at least one air inlet in the lid and a second connection surface of the housing which is provided opposite the lid also passes the drug. Hereby inhalation air can be used for providing the drug into a form suitable for inhalation and for transferring the drug through the pacifier.

In some embodiments of the invention at least one separate air channel is provided in the housing part, wherein said at least one separate air channel is provided in fluid connection to at least one open air inlet of the housing part which is not in communication with a drug compartment of the housing where the drug initially is provided and wherein said open air inlet is open for passage of air in both directions. Hereby a user of the pacifier can both inhale and exhale through the pacifier.

In some embodiments of the invention said housing of said housing part comprises a pressurized chamber and/or a biased resilient member which can be activated for providing a pressure to the drug for transferring the drug to the passageway of the suction part, possibly via a drug preparation device. Hereby an additional pressure can be provided which may be suitable for forcing the drug through an aerosolization membrane.

In some embodiments of the invention said pressurized chamber comprises a releasing device, whereby said releasing device can be moved by an air flow provided through the pacifier during inhalation by a user, whereby said pressurized chamber is activated by a movement of said releasing device for providing a pressure to the drug for transferring the drug to the passageway of the suction part, possibly via a drug preparation device. Hereby an inhalation-controlled drug-release is provided.

In some embodiments of the invention said housing further comprises a drug compartment comprising a bottom with attached side walls, wherein said side walls comprises openings through which the drug which is held in said drug compartment can be released, whereby said drug compartment further comprises a movable cover which can move into at least two positions whereby in a first position said movable cover covers said openings such that the drug is kept inside the drug compartment and in a second position said movable cover does not cover said openings such that the drug can escape through said openings, whereby said movable cover is forced into said first position by a connected resilient device and whereby an air flow through the pacifier during inhalation by a user of the pacifier will force the movable cover into said second position.

Further embodiments are described in the dependent claims and in the detailed description.

BRIEF DESCRIPTION OF THE DRAWINGS

FIG. 6*a* is a cross section of a suction part according to one embodiment of the invention. FIGS. 6*b* and 6*c* are cross sections of a pacifier comprising the suction part as shown in FIG. 6*a* and a housing part as shown in FIGS. 4*a*-4*c*.

DETAILED DESCRIPTION OF EMBODIMENTS

Figures 14A, 14B:
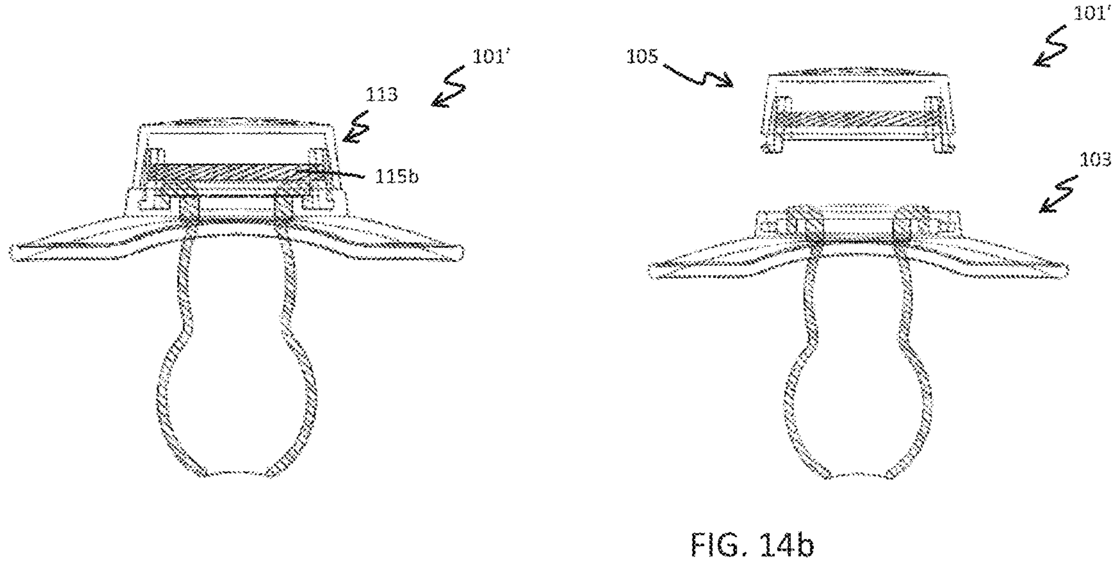
FIG. 14*a* shows schematically in cross section a pacifier comprising a filter device in an assembled position.
FIG. 14*b* shows the same pacifier as in FIG. 14*a* but in a separated position.
Figure 15:
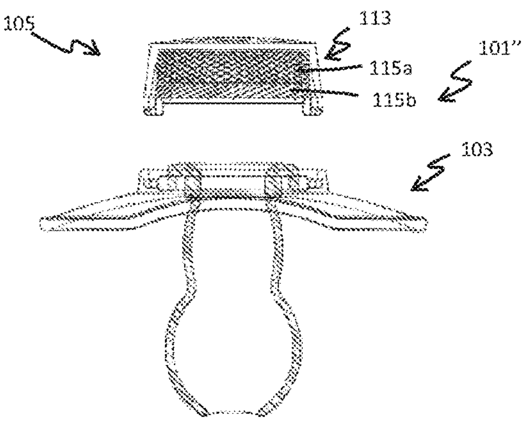
FIG. 15 shows schematically in cross section a pacifier comprising both a HME device and a filter device in a separated position.
Figure 16A:
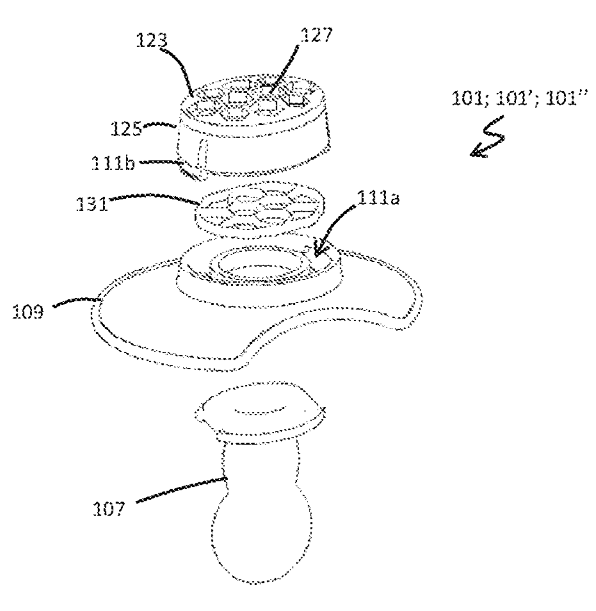
FIGS. 16*a* and 16*b* show two different alternatives of connections between the housing part and suction part.
Figure 16B:
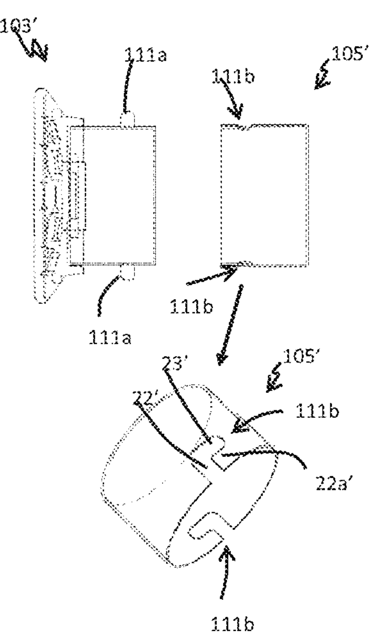
Figure 17:
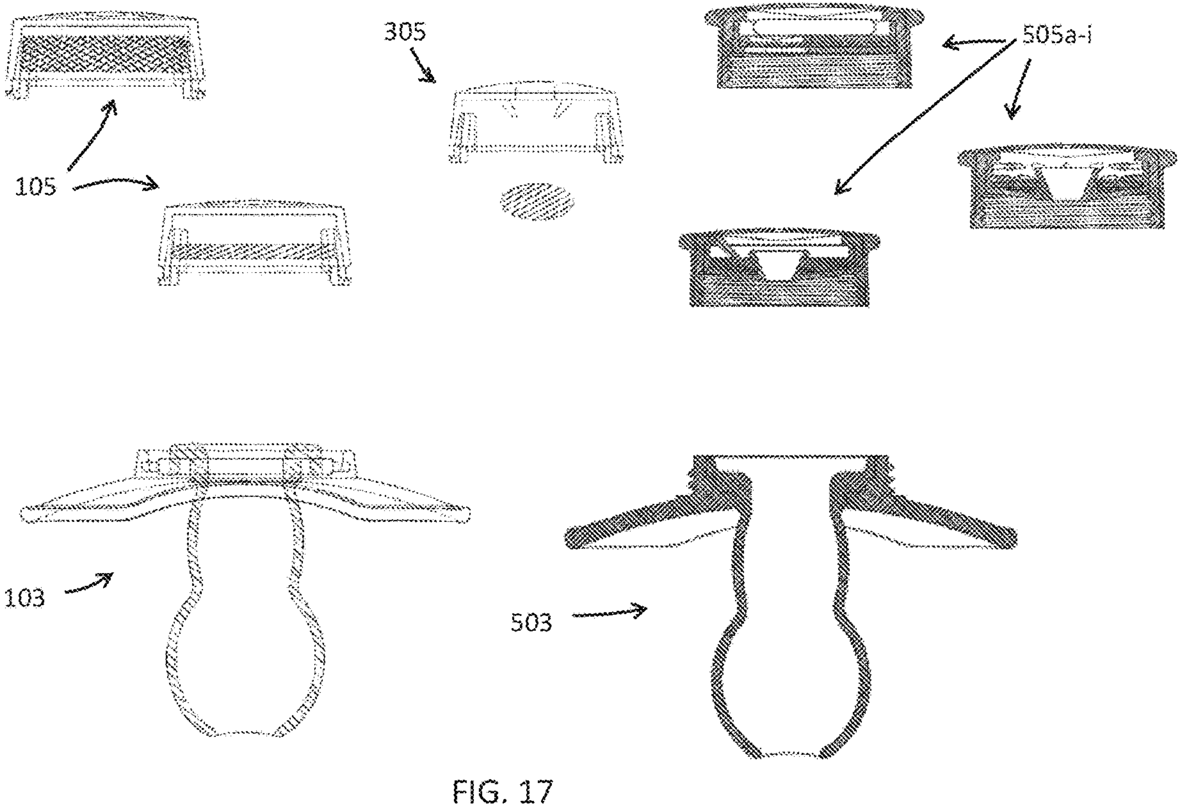
FIG. 17 show some examples of a pacifier system according to the invention.

In FIGS. 1-11 a number of different embodiments of pacifiers comprising a drug to be inhaled through the pacifier according to the invention are shown. Some of the details are the same or corresponding between the different embodiments and are also given the same or corresponding reference numbers. In FIGS. 1-3 the drug is a powder drug to be inhaled. In FIGS. 4, 7, 8, 9 and 10 the drug is a liquid drug for inhalation and the pacifier comprises an aerosolization device for transforming the liquid drug into a form for inhalation. In FIG. 11 the drug can be either a powder drug or a liquid drug which is aerosolized. The different embodiments will be further described below with reference to each specific drawing but first a general description of the invention is given with reference to all the drawings 1-11. FIGS. 12*a*, 12*b*, 16*a* and 16*b* show alternative connection possibilities between a suction part and a housing part. FIGS. 13-15 show a pacifier comprising a HME and/or a filter device and will be described further below. FIG. 17 show a pacifier system according to the invention and will be described further below.

According to the invention a pacifier 501*a*-501*i* comprising a suction part 503; 503'; 503"; 103 and a housing part 505*a*-505*i* is provided. The suction part 503; 503'; 503"; 103 comprises a nipple 107 and a shield 109 connected to each other. The suction part 503; 503'; 503"; 103 comprises further a passageway 117 through which a fluid can pass from outside a mouth of a user of the pacifier to inside the mouth of the user of the pacifier. The passageway 117 passes through the nipple 107 and the shield 109. The housing part 505*a*-505*i* comprises a housing 113, wherein said housing 113 is arranged to be prefilled with a drug 510; 510' which can pass through the passageway 117 into the mouth of the user when the housing part 505*a*-505*i* is connected to said suction part 503; 503'; 503"; 103 and wherein said drug 510; 510' is a drug to be inhaled through the passageway 117 of the suction part 503; 503'; 503"; 103. The housing 113 of the housing part 505*a-i* is prefilled with the drug 510; 510' and comprises hereby the drug 510; 510'.

In some embodiments of the invention the suction part 503; 503'; 503"; 103 is a reusable part and the housing part 505*a*-505*i* is an exchangeable part, wherein said reusable suction part 503; 503'; 503"; 103 and said exchangeable housing part 505*a*-505*i* are releasably connectable to each other. Therefore the suction part 503; 503'; 503"; 103 comprises in these embodiments at least one first connection device 111*a* and said housing part 505*a*-505*i* comprises at least one second connection device 111*b* which is releasably connectable to the at least one first connection device 111*a*. In all the embodiments as shown in FIGS. 1-17 the suction part 503; 503'; 503"; 103 and the housing part 505*a*-505*i* are releasably connected to each other. However, in another embodiment the suction part and the housing part can be provided connected to each other, i.e. not releasably connected to each other. Most of the details described below can be provided also for such a connected pacifier embodiment which will be apparent for a skilled person.

In all the embodiments shown said housing 113 comprises at least one air inlet 541; 541', whereby air can be drawn into the housing 113 through said air inlet 541; 541' and further through said passageway 117 by a user of the pacifier 501*a*-501*i* when the user is inhaling through the passageway 117 of the suction part 503; 503'; 503"; 103. However, such an air inlet provided in the housing may not be necessary in all embodiments. For example, a pressurized chamber or a biased resilient member can be used for forcing the drug through the passageway of the pacifier.

In the embodiments as shown in FIGS. 1-9, but not necessarily for the invention, the housing 113 comprises at least one air inlet 541 which is provided with at least one valve 543 such that passage of air via said at least one air inlet 541 only is admitted into and not out from said housing 113. Hereby air can be inhaled via said air inlet 541 by a user of the pacifier and this air can be passing an interior space 121 of the housing 113 where the drug 510; 510' is provided. Hereby, in these embodiments, the air is passing the drug which together with a drug preparation device 551; 551' provided in said housing part 505*a*-505*i* will provide the drug to the user in a form suitable for inhalation. However, in some embodiments of the invention inhaled air will not be passing the drug. Air can also in some embodiments of the invention be inhaled through the housing but be passing outside a drug compartment 573 which will be further described below. The drug preparation device 551; 551' is hereby configured for transferring the drug 510; 510' to the suction part 503; 503'; 503"; 103 in a form for inhalation and can be designed in different ways. A few different possible designs of a drug preparation device 551; 551' are described below with reference to the different drawings.

Figures 1A, 1B, 1C, 1D:
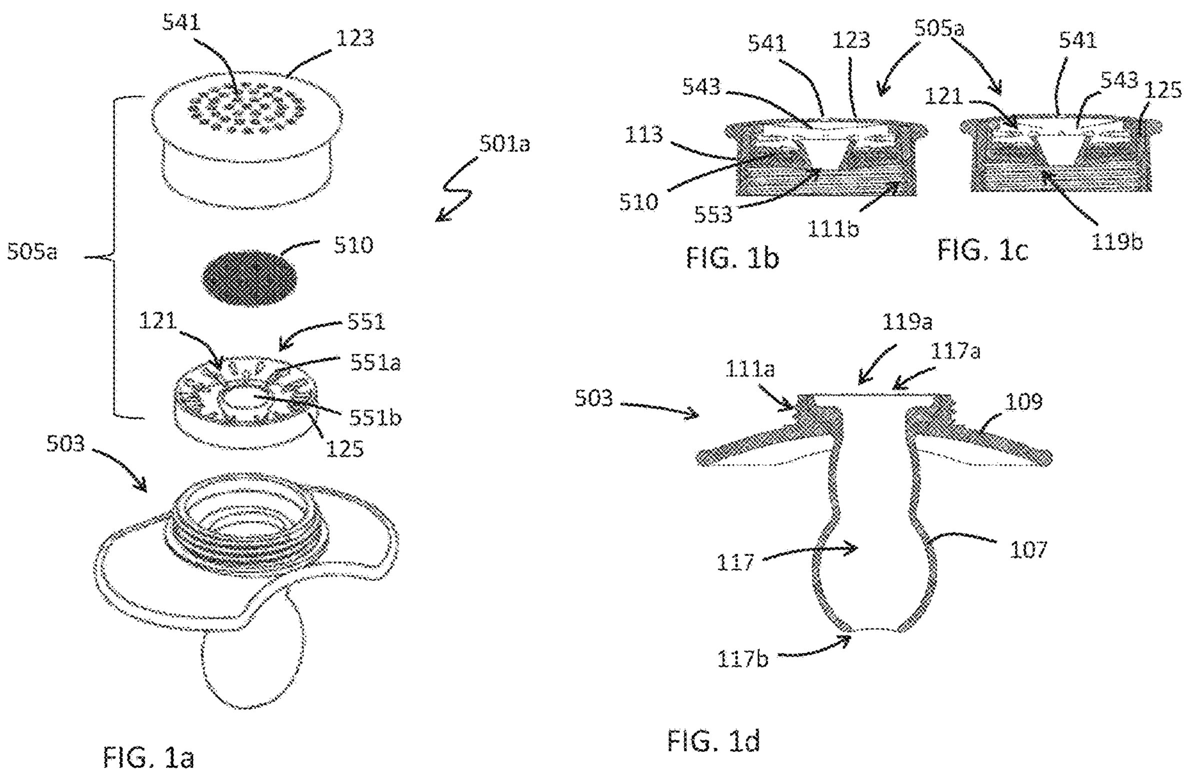
FIG. 1*a* is an exploded view in perspective of a pacifier according to one embodiment of the invention.
FIGS. 1*b* and 1*c* are cross sections of a housing part of the pacifier as shown in FIG. 1*a* in two different positions.
FIG. 1*d* is a cross section of a suction part of the pacifier as shown in FIG. 1*a*.

The valve 543 connected to the air inlet 541 can be seen in two different positions, one open and one closed position in FIG. 1*b* (closed position), 1*c* (open position) and in the same way in FIGS. 2*b*, 2*c*, 3*b*, 3*c*, 4*b*, 4*c*, 7*b*, 7*c* and 8*b*, 8*c*.

Figures 7A, 7B, 7C, 7D:
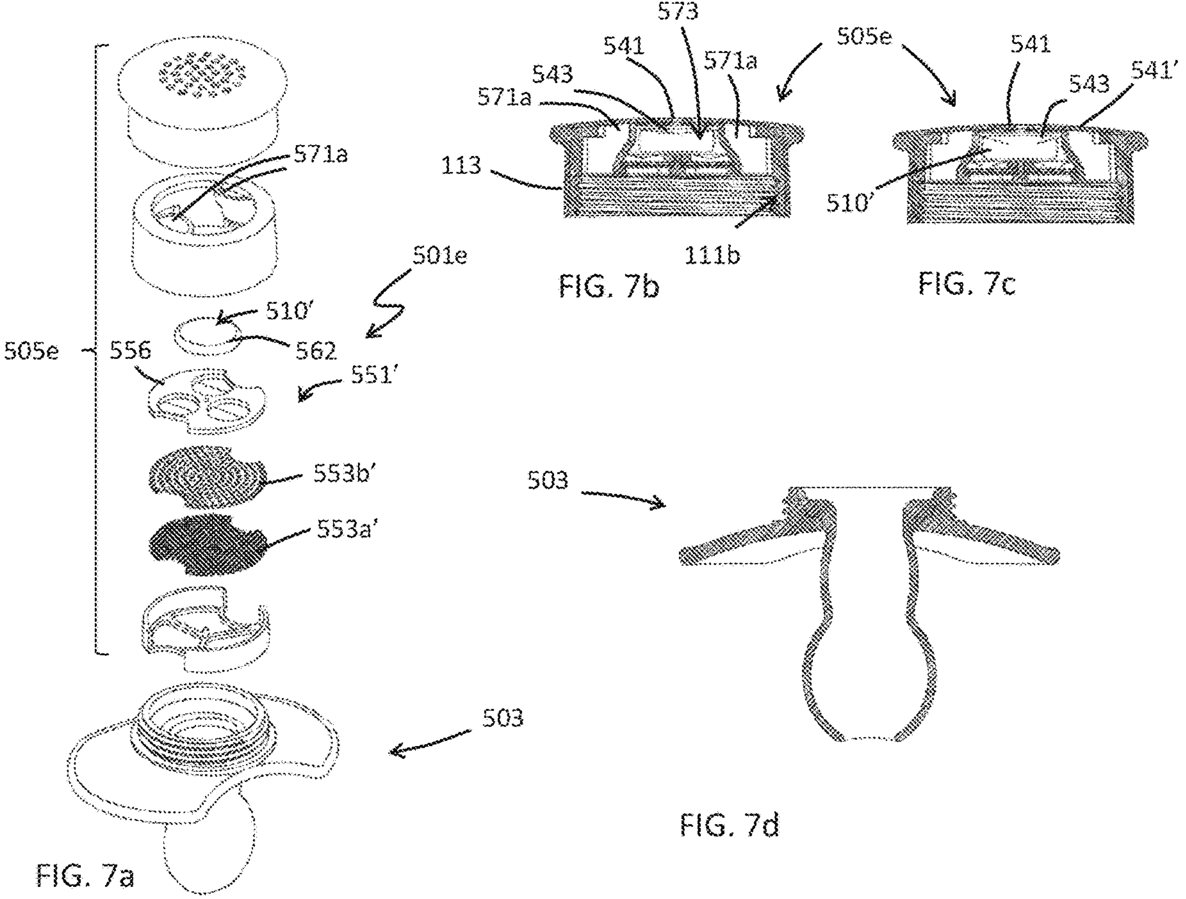
FIG. 7*a* is an exploded view in perspective of a pacifier according to another embodiment of the invention.
FIGS. 7*b* and 7*c* are cross sections of a housing part of the pacifier as shown in FIG. 7*a* in two different positions.
FIG. 7*d* is a cross section of a suction part of the pacifier as shown in FIG. 7*a*.
Figures 8A, 8B, 8C, 8D, 8E:
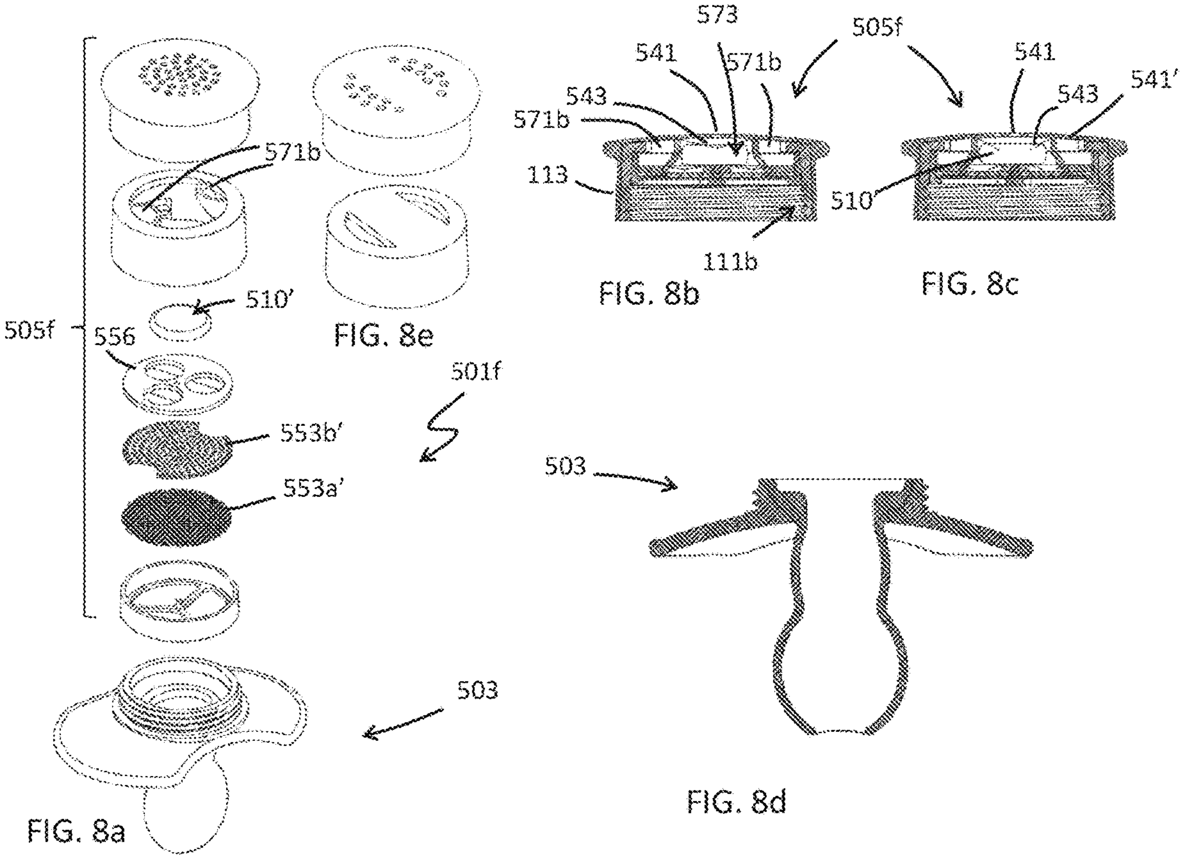
FIG. 8*a* is an exploded view in perspective of a pacifier according to another embodiment of the invention.
FIGS. 8*b* and 8*c* are cross sections of a housing part of the pacifier as shown in FIG. 8*a* in two different positions.
FIG. 8*d* is a cross section of a suction part of the pacifier as shown in FIG. 8*a*.
FIG. 8*e* is an exploded view in perspective of a part of a pacifier according to another embodiment of the invention.
Figures 9A, 9B, 9C:
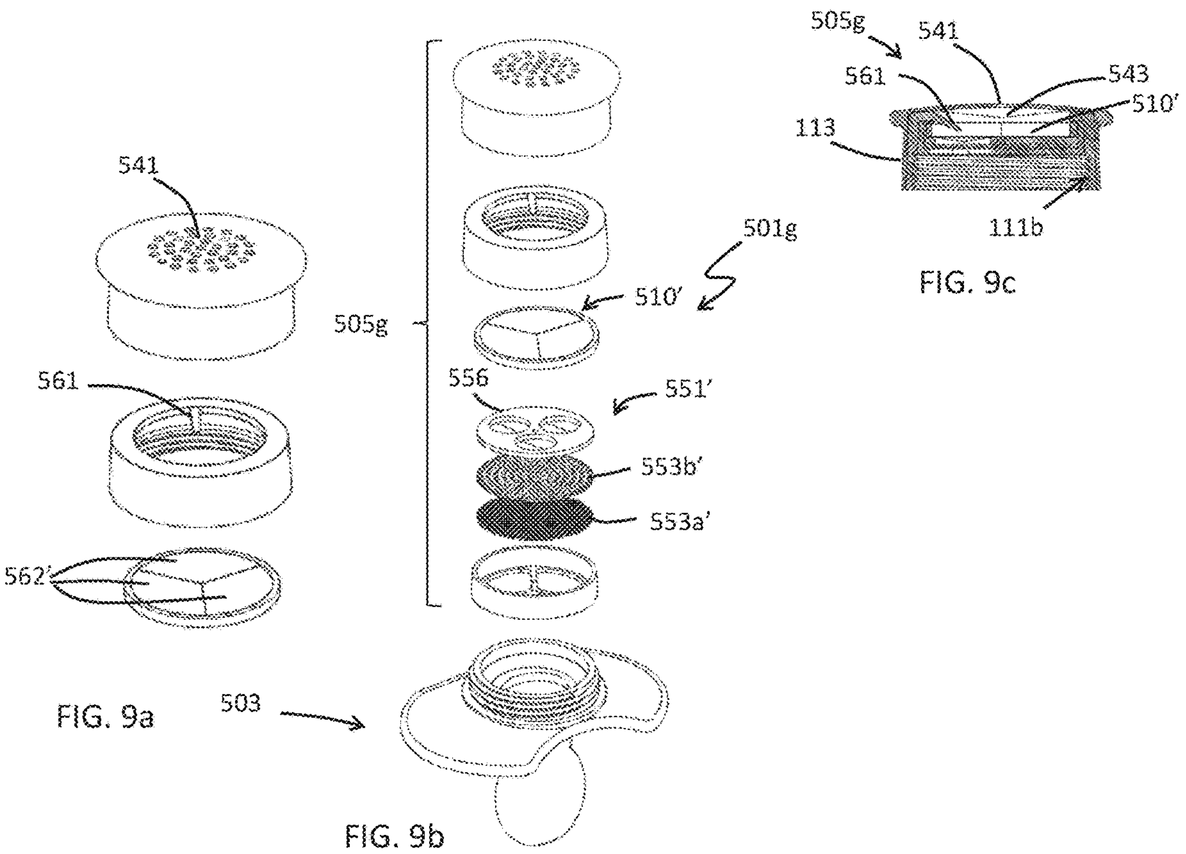
FIG. 9*a* is an exploded view in perspective of a part of a pacifier according to another embodiment of the invention which can be used together with any of the previous described embodiments.
FIG. 9*b* is an exploded view in perspective of a pacifier according to one embodiment of the invention using the parts as shown in FIG. 9*a*.
FIG. 9*c* is a cross section of a housing part of the pacifier as shown in FIG. 9*b*.

An air inlet 541' which is open in both directions, i.e. not connected to a valve, is provided in some of the embodiments. In for example the embodiments shown in FIGS. 7 and 8 and 10 at least one air inlet 541' is provided separated from a drug compartment 573 which is provided inside the housing part 505*e-f, h, h'* and in which drug compartment 573 the drug 510' is provided. Hereby air can be passing in both directions through the pacifier but not passing the drug 510' and hereby the user of the pacifier can both inhale and exhale via the pacifier. In these embodiments as shown in FIGS. 7 and 8 and 10 at least one separate air channel 571*a*; 571*b* is furthermore provided in the housing part 505*e*, 505*f*, 505*h*, 505*h'* wherein said at least one separate air channel 571*a*; 571*b* is provided in fluid connection to the at least one open air inlet 541' of the housing part 505*e*, 505*f*, 505*h*, 505*h'* which is not in communication with the drug compartment 573 of the housing 113 where the drug initially is provided and wherein said open air inlet 541' is open for passage of air in both directions. In FIGS. 7*a*-7*d* an embodiment is shown where the separate air channels 571*a* are completely separated from the drug throughout the whole pacifier and in FIGS. 8*a*-8*d* an embodiment is shown where the separate air channels 571*b* are provided only through a part of the housing part 505*f* whereby the inhaled air can be used for transferring the drug into a suitable state for inhalation and transport the drug to the desired part of the respiratory system.

In FIGS. 1*a*-1*d* some features which are common for most of the embodiments are given reference numbers and will now be described. The passageway 117 comprises a first end 117*a* and a second end 117*b* between which a fluid can pass, which first end 117*a* is provided at a first connection interface 119*a* of the suction part 503; 503', 503"; 103 configured for mating with a second connection interface 119*b* of the housing part 505*a-i* for embodiments where the suction part and the housing part are releasably connected. The second end 117*b* of the passageway 117 is provided in a part of the nipple 107 which is configured to be positioned within a user's mouth during use of the pacifier 501*a-i*, whereby a fluid can pass through the passageway 117 between the first connection interface 119*a* of the suction part 503; 503'; 503"; 103 and the inside of a user's mouth during use of the pacifier.

Furthermore, the housing 113 of the housing part 505*a-i* comprises an interior space 121 which is defined by a lid 123, surrounding walls 125 and the second connection interface 119*b* which is provided opposite the lid 123. The lid 123 may comprise the at least one air inlet 541; 541' if air inlets are provided. The drug 510; 510' is provided within the interior space 121 of the housing 113 such that air passing between the at least one air inlet 541 in the lid 123 and the second connection surface 119*b* of the housing 113 also, in some embodiments passes the drug. The interior space 121 or a part of the interior space 121 is also called a drug compartment 573, see for example FIGS. 7*b* and 8*b*. The drug 510; 510' is provided within the interior space 121 (and within the drug compartment 573) of the housing 113. In some embodiments of the invention the drug 510; 510' is provided inside a capsule 562 having a breakable capsule cover. The second connection interface 119*b* of the housing part 505*a-i* may be covered by a protective cover (not shown) like for instance a thin aluminium film or similar to protect the drug from contamination, from leaking and to ensure its shelf half-life. This can either be teared off by the user before use or be automatically teared open when the housing part and suction part are connected, for example by a protruding tearing device provided in the housing part or in the suction part.

Figures 2A, 2B, 2C, 2D:
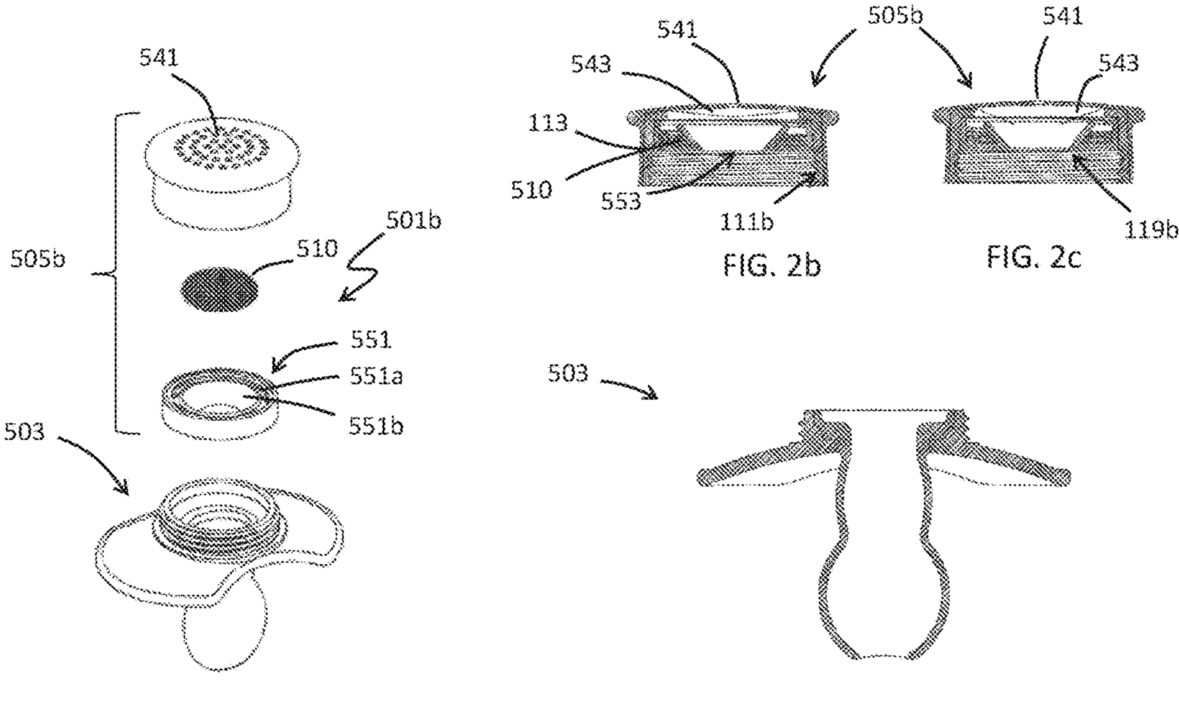
FIG. 2*a* is an exploded view in perspective of a pacifier according to another embodiment of the invention.
FIGS. 2*b* and 2*c* are cross sections of a housing part of the pacifier as shown in FIG. 2*a* in two different positions.
FIG. 2*d* is a cross section of a suction part of the pacifier as shown in FIG. 2*a*.
Figures 3A, 3B, 3C, 3D:
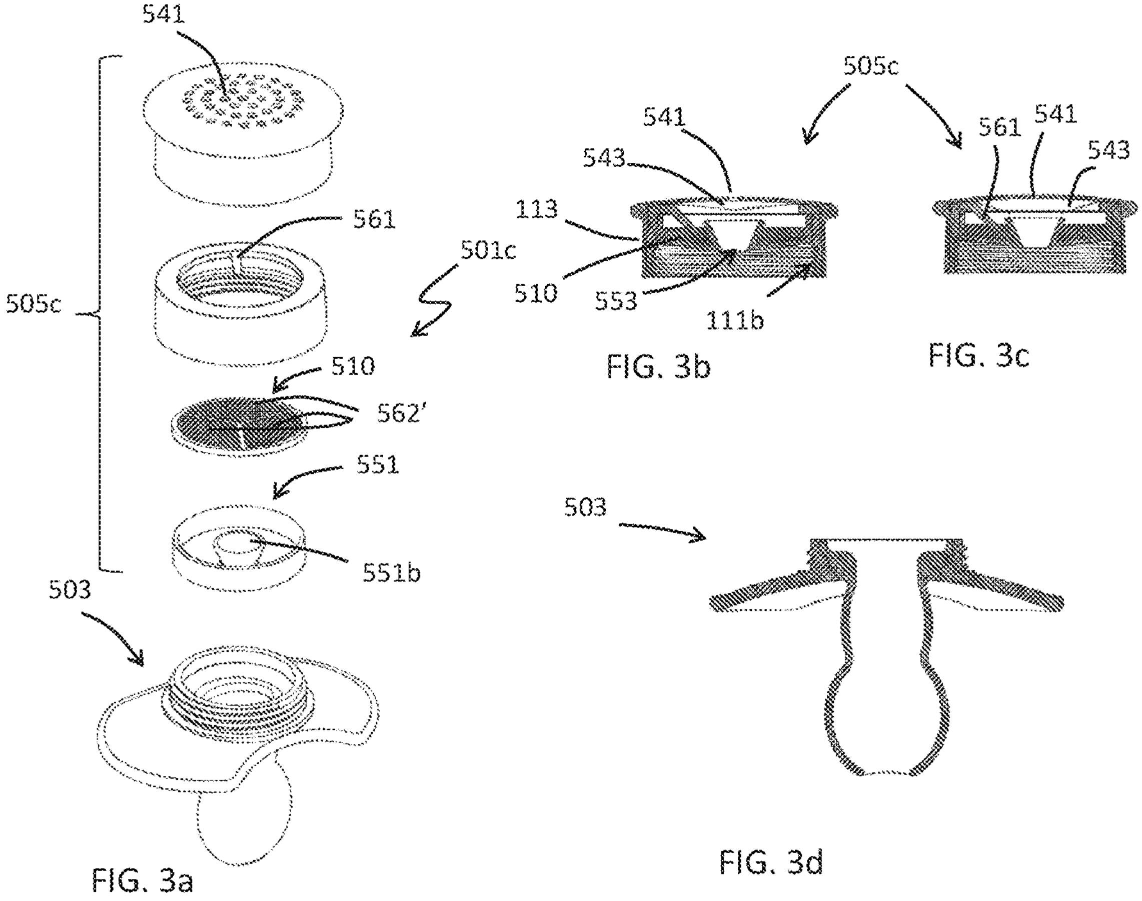
FIG. 3*a* is an exploded view in perspective of a pacifier according to another embodiment of the invention.
FIGS. 3*b* and 3*c* are cross sections of a housing part of the pacifier as shown in FIG. 3*a* in two different positions.
FIG. 3*d* is a cross section of a suction part of the pacifier as shown in FIG. 3*a*.

In the embodiments shown in FIGS. 1-3 the drug 510 is a powder drug for inhalation and said drug preparation device 551 comprises a turbulence device 551*a* and a dosing device 551*b*. Said turbulence device 551*a* can for example be spikes which are distributed in an inner volume of the housing 113 where the drug is provided as a powder as shown in FIGS. 1*a*-1*c* and/or a coil provided in an inner volume of the housing where the powder drug is provided as shown in FIGS. 2*a*-2*c*. When a user inhales through the pacifier the air will, thanks to the spikes and/or the coil, provide a turbulence inside the housing 113 which will distribute the powder drug in a suitable way. The dosing device 551*b* can be a funnel provided in a centre part of the housing and having an opening 553 (seen in FIGS. 1*b*, 2*b*, 3*b*) towards the suction part 503. The funnel can be dimensioned in relation to the turbulence device 551*a* and in relation to the specific drug such that a suitable amount of the drug will pass through the funnel into the passageway 117 of the suction part 503 in each inhalation from the user.

In FIGS. 4, 7, 8, 9 and 10 the drug 510' is a liquid drug for inhalation and said drug preparation device 551' comprises an aerosolization device 551*a*'. The aerosolization device 551*a*' will transform the liquid drug 510' into an aerosol which can be inhaled. A valve membrane 556 comprising one or more valves 557 (three valves 557 are shown in the embodiments of FIGS. 4, 7, 8 and 9 but any number is possible) can be provided between the drug 510' and the aerosolization device 551*a*'. The valves 557 in the valve membrane 556 will only be opened during inhalation and closed otherwise. Hereby the drug 510' can be kept inside the housing 113 until a user of the pacifier starts to inhale.

Figures 10A, 10B, 10C:
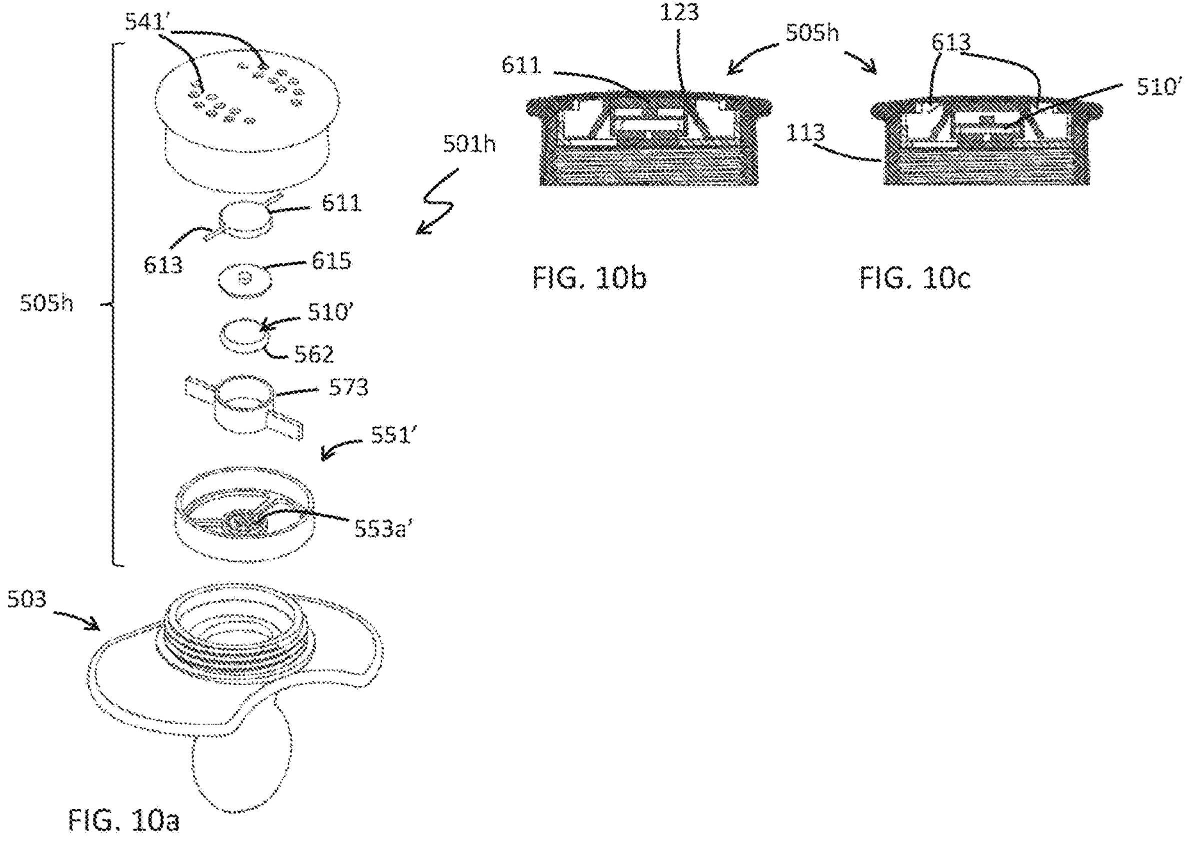
FIG. 10*a* is an exploded view in perspective of a pacifier according to another embodiment of the invention.
FIGS. 10*b* and 10*c* are cross sections of a housing part of the pacifier as shown in FIG. 10*a* in two different positions.
Figure 10D:
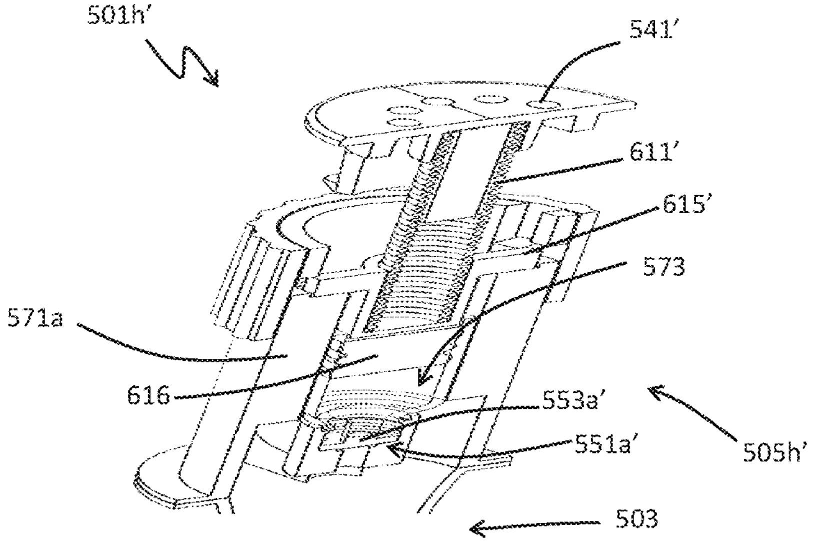
FIG. 10*d* is an exploded view in cross section of a pacifier according to another embodiment of the invention.
Figures 10E, 10F:
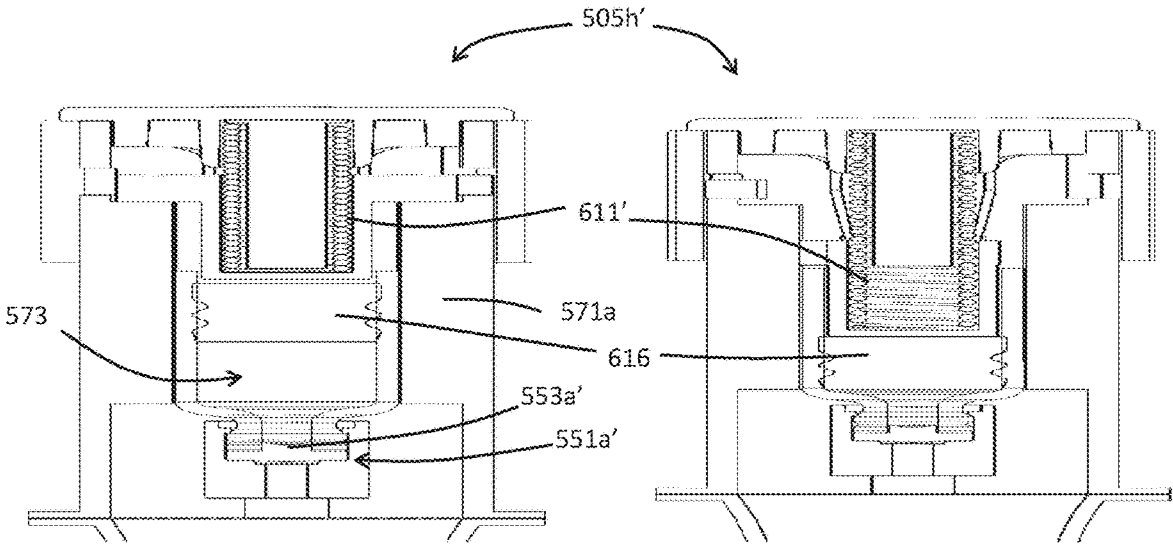
FIGS. 10*e* and 10*f* are cross sections of a housing part of the pacifier as shown in FIG. 10*d*.

In some embodiments the aerosolization device 551*a*' comprises one or more aerosolization membranes 553*a*', 553*b*'. The aerosolization membranes can be a fine pore membrane 553*a*' and/or an oscillating membrane 553*b*', whereby said liquid drug 510' will be aerosolized when forced through said one or more aerosolization membranes 553*a*'; 553*b*'. Inhalation by a user of the pacifier 501*d-g* and/or a pressurized chamber 611 and/or a biased force such as from a biased spring provided in the pacifier 501*h*, 501*h*' will force the liquid drug through the one or more aerosolization membranes 553*a*'; 553*b*'. In some embodiments an additional pressure for forcing the liquid drug through the one or more aerosolization membranes 553*a*'; 553*b*' is provided. Such an additional pressure can for example be provided by a pressurized chamber 611 as shown in FIGS. 10*a-c* or by a resilient member as shown in FIGS. 10*d-f*. This will be further described below. The sizes of the pores in the fine pore membrane 553*a*' and the thickness of the membrane will decide the size of the aerosol droplets which are then inhaled, this size is important for where the droplets are then deposited in the respiratory tract.

Figures 4A, 4B, 4C, 4D, 4E:
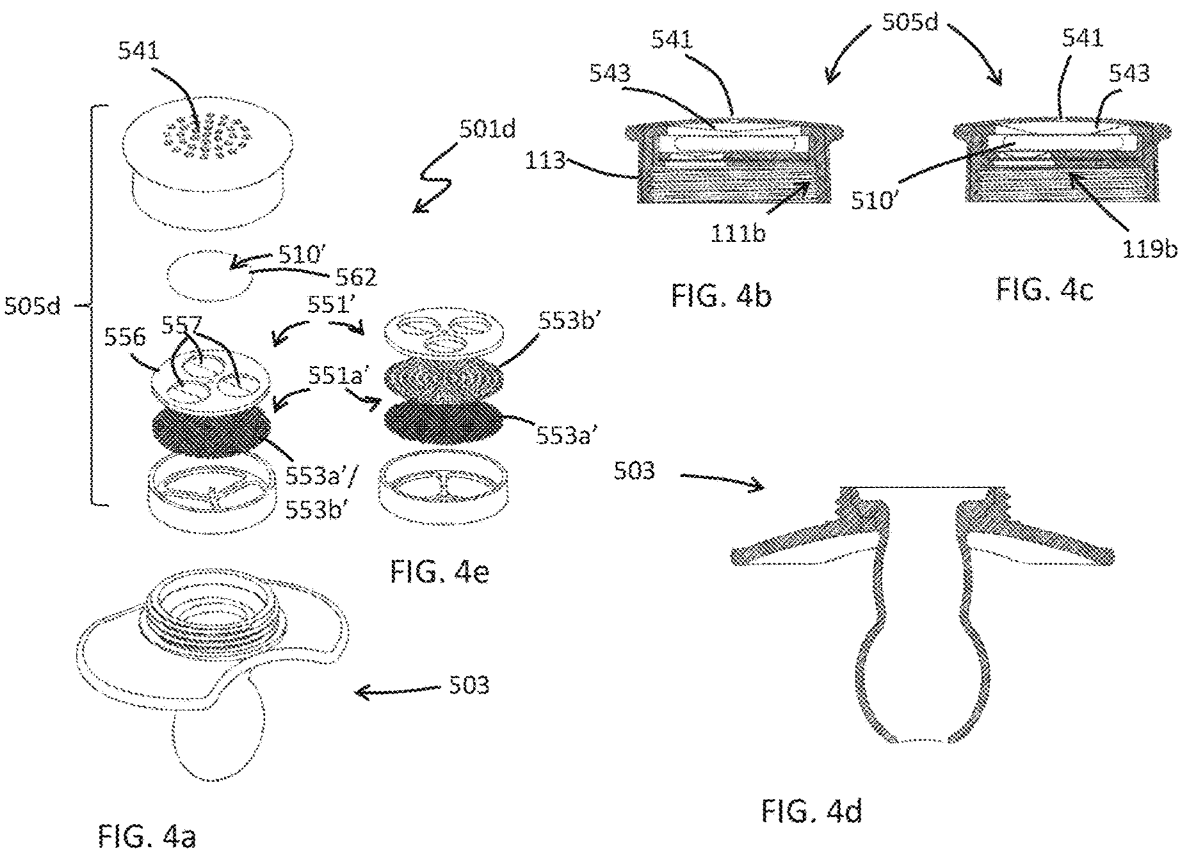
FIG. 4*a* is an exploded view in perspective of a pacifier according to another embodiment of the invention.
FIGS. 4*b* and 4*c* are cross sections of a housing part of the pacifier as shown in FIG. 4*a* in two different positions.
FIG. 4*d* is a cross section of a suction part of the pacifier as shown in FIG. 4*a*.
FIG. 4*e* is an exploded view in perspective of a part of a pacifier according to another embodiment of the invention.

In some embodiments the aerosolization device 551*a*' comprises an oscillating membrane 553*b*'. This could be in combination with the fine pore membrane 553*a*' or alone. In FIG. 4*a* an embodiment of the invention is shown where the aerosolization device 551*a*' comprises only one aerosolization membrane, which can for example be either a fine pore membrane 553*a*' or an oscillating membrane 553*b*'. Other types of aerosolization membranes may also be possible to use. In FIG. 4*e* an embodiment of the invention is shown where the aerosolization device 551*a*' comprises both an oscillating membrane 553*b*' and a fine pore membrane 553*a*'. If the oscillating membrane 553*b*' is in combination with the fine pore membrane 553*a*' (as shown in FIGS. 4*e*, 7*a*, 8*a* and 9*b*) the oscillating membrane 553*b*' should be provided between the fine pore membrane 553*a*' and the valve membrane 556, i.e. the drug will during inhalation first come to the oscillating membrane 553*b*' and after having passed the oscillating membrane 553*b*' the drug will come to the fine pore membrane 553*a*'. Said oscillating membrane 553*b*' is configured for starting to oscillate when a user of the pacifier inhales whereby the liquid drug will be aerosolized by said oscillations and whereby said oscillating membrane 553*b*' comprises pores which are of a size such that aerosolized drug can pass through the oscillating membrane 553*b*' and further through the housing part 505*d-i* to either the fine pore membrane 553*a*' or to the passageway 117 of the suction part 503; 503'; 503"; 103. The sizes of the pores and the thickness of the membrane will decide the size of the aerosol droplets which are then inhaled, this size is important for where the droplets are then deposited in the respiratory tract.

In some embodiments of the invention the drug 510; 510' can be provided inside a drug capsule 562; 562'. The drug capsule 562 may have a breakable capsule cover whereby the drug capsule 562 can have a size such that the drug capsule 562 will be compressed and broken when the suction part 503; 503'; 503", 103 and the housing part 505*a-i* are connected.

Figures 5A, 5B, 5C, 5D:
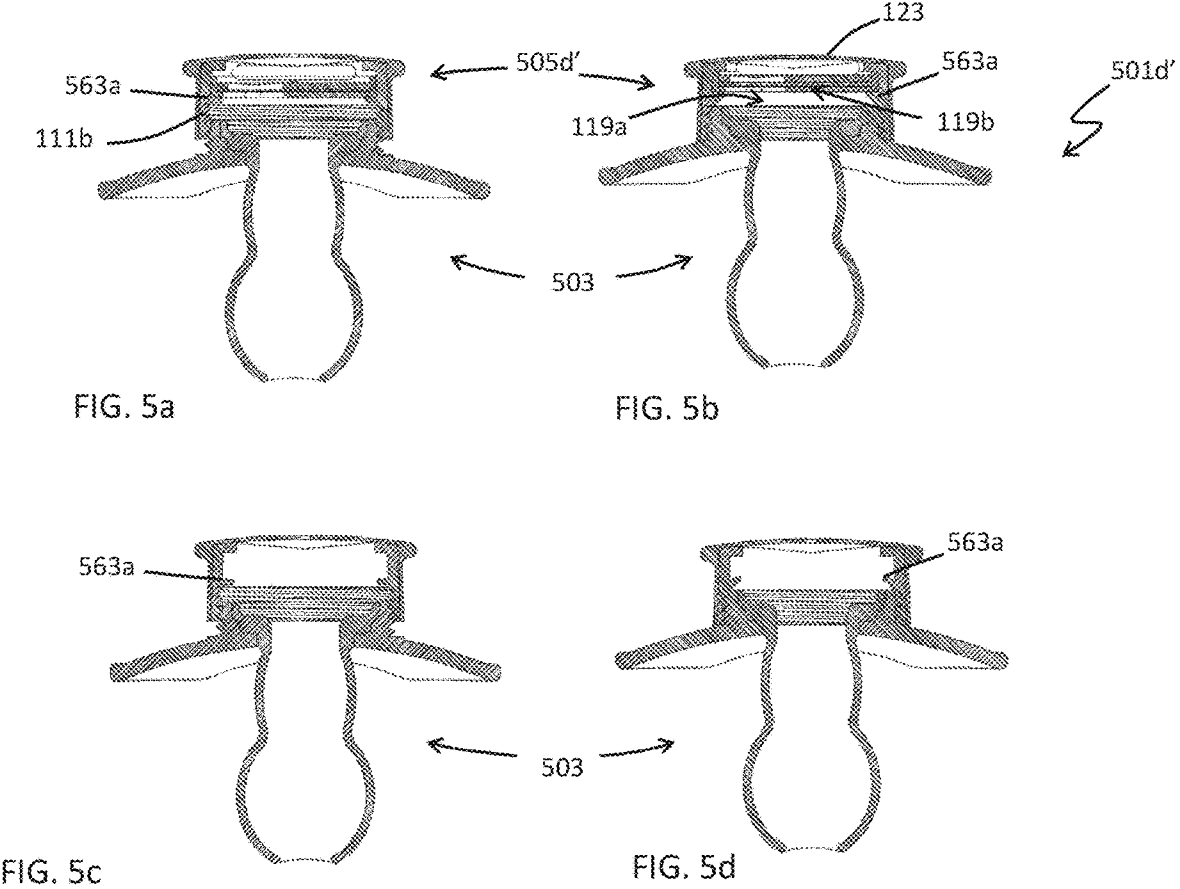
FIG. 5*a* and FIG. 5*b* are cross sections of a pacifier according to another embodiment of the invention in two different positions.
FIGS. 5*c* and 5*d* correspond to FIGS. 5*a* and 5*b* but with some details removed.

The first and second connection device 111*a*, 111*b* of the suction part 503; 503'; 503"; 103 and the housing part 505*a-i* can be threaded connection devices 111*a*, 111*b* as shown in FIGS. 1-11. However, other connection devices 111*a*, 111*b* are of course possible. In FIG. 12*a* an alternative connection device 111*a* is shown which provides a snap connection with rotation locking of the housing part to the suction part. In FIG. 12*b* another snap connection alternative is shown where either the first or the second connection device 111*a*, 111*b* comprises protruding parts and the other comprises recesses into which the protruding parts can be received. In FIGS. 16*a* and 16*b* two other connection devices comprising a rotation lock are shown. All these alternative connection devices are further described below. In FIGS. 5 and 6 features of the invention which will provide a possibility to compress an interior space 121 within the housing 113, possibly for breaking a drug capsule 562 and releasing the drug 510', are described. This is described with reference to the connection device comprising threads. Other connection devices as described above are however also possible. The housing part 505*a-i* or the suction part 503; 503'; 503"; 103 may comprise at least one protruding part 563*a*, 563*b*. The at least one protruding part 563*a*, 563*b* may be provided to the first or second connection devices 111*a*, 111*b*. The at least one protruding part 563*a*, 563*b* will push the second connection interface 119*b* towards the lid 123 when the housing part 505*a-i* and the suction part 503; 503', 503"; 103 are connected whereby a pressure will be provided to the interior space 121. Hereby a drug capsule 562 may be broken by said pressure and the drug 510' is released. Beside this possibility to break the drug capsule containing drugs the volume reduction in the interior space 121 leads to an increased pressure in the interior space. This pressure can then be utilized to drive liquid drug through the aerosolization membrane 553*a*'. In one embodiment this pressure release can be inhalation controlled. In FIGS. 5*a*-5*b* a protruding part 563*a* is provided to the second connection device 111*b*, i.e. to the housing part. The protruding part 563*a* is in this embodiment provided at an inner surface of the housing 113 pointing towards a centre of the housing 113 before connection of the suction part and the housing part. The protruding part 563*a* is provided at a position such that when the suction part and the housing part are connected the connection device 111*a* of the suction part will press the protruding part 563*a* in a direction towards the lid 123 of the housing part. Hereby the at least one protruding part 563*a* is flexible to some extent. When the protruding part 563*a* changed direction and points towards the lid 123, as shown in FIG. 5*b* (and in FIG. 5*d* in a simplified view without internal components), the second connection interface 119*b* of the housing part will be pressed closer to the lid 123 whereby a volume of the interior space 121 will decrease and a drug capsule 562 may be broken for releasing the drug and the pressure is increased in the interior space/drug compartment 121/573. In FIGS. 6*a*-6*c* another alternative is shown where a protruding part 563*b* is provided to the suction part 503'. The at least one protruding part 563*b* is in this example protruding towards a lid 123 of the housing part. In FIG. 6*b* a first connection state is shown before the suction part and the housing part are completely connected. The protruding part 563*b* will accomplish a compression of the interior space 121 when the connection is completed as is seen in FIG. 6*c*.

In some embodiments of the invention, as shown in FIGS. 3 and 9, the housing part 505*c*, 505*g* further comprises a piercing member 561 arranged for piercing a drug capsule 562; 562', in which said drug 510; 510' may be provided, when said housing part 505*c*; 505*g* is provided in a certain position in relation to the suction part 503; 503', 503"; 103 hereby allowing the drug 510; 510' to be released at a certain moment. A user of the pacifier or a supervisor of the user of the pacifier can provide the housing part in the right position in relation to the suction part for piercing the drug capsule 562, 562' when the user is ready for drug inhalation. A right position for piercing could be provided for example by rotating the housing part in relation to the suction part.

In some embodiments of the invention said drug 510; 510' can be provided in more than one drug capsule 562' and said housing part 505*c*, 505*g* can be provided in more than one different positions in relation to the suction part 503; 503', 503"; 103 whereby said piercing member 561 will be piercing one drug capsule 562' in each of said positions.

In FIGS. 10*a*-10*c* an embodiment of the invention is shown wherein the housing part 505*h* of the pacifier 501*h* comprises a pressurized chamber 611 which can be activated for providing a pressure to the drug 510; 510', wherein said pressurized chamber 611 comprises a releasing device 613. The releasing device 613 can be moved by an air flow provided through the pacifier during inhalation by a user, whereby said pressurized chamber 611 is activated by a movement of said releasing device 613 for providing a pressure to the drug for transferring the drug to the passageway 117 of the suction part 503; 503', 503"; 103, possibly via a drug preparation device 551; 551'. The releasing device 613 is here shown to be two protruding parts, however the number can of course be different. The protruding parts will deflect towards the suction part during inhalation and the pressurized chamber 611 will then be activated. A pressure transferring device 615 in the form of a plate or piston will be forced towards the drug 510' by the pressure released form the pressurized chamber 611 whereby the drug capsule 562 will be compressed, which is seen in FIGS. 10*b* and 10*c*.

In this embodiment of the invention the inhaled air need not be passing the drug 510'. The pressurized chamber 611 will instead provide the necessary pressure for forcing the drug 510' through the drug preparation device 551; 551', which in this example is a fine pore membrane 553*a'*. The fine pore membrane 553*a'* is here provided in a centre part of the housing 113 and a drug compartment 573, in which the drug initially is provided, will guide the drug towards the fine pore membrane 553*a'* while inhalation and exhalation air is guided through a volume of the pacifier surrounding said drug compartment 573 and surrounding said fine pore membrane 553*a'*. Air inlets 541' are provided in the lid 123 and they can in this embodiment be provided in an area outside a central part. This contraption of the device allows for inhalation-controlled drug-release.

In FIGS. 10*d*-*f* an embodiment of the invention is shown wherein the housing part 505*h'* of the pacifier 501*h'* comprises a resilient member 611', such as for example a spring, which is biased when mounted in the housing part 505*h'*. The resilient member 611' can be released by for example a rotation of a part of the housing part 505*h'* whereby a locking member 617 can be released and thereby releasing the resilient member 611'. A pressure transferring device 615' in the form of a plate or piston will be forced by the resilient member 611' against a movable plug 616 provided in the drug compartment 573. The plug 616 is hereby forced by the resilient member 611' into the drug compartment 573 whereby the inner volume of the drug compartment 573, where the drug is provided, is decreasing. Hereby a pressure inside the drug compartment 573 is increasing and the drug which in this embodiment is a liquid drug is forced through the drug preparation device 551' which in this embodiment is an aerosolization device 551*a'* which in this embodiment is a fine pore membrane 553*a'*. Hereby the liquid drug will be aerosolized and it will be passed over to the suction part 503 (only shown in part in this drawing) of the pacifier 501*h'* for inhalation by the user. In this embodiment inhalation from the user is not needed for the drug preparation. Inhalation through the pacifier 501*h'* is possible via the air inlets 541' and via a separate air channel 571*a*. However, the inhaled air will not pass the drug compartment 573 in this embodiment of the invention. A valve, for example a rotating impeller like valve, can possibly also be provided in this embodiment between the drug preparation device 551' and the suction part 503 of the pacifier. This valve can be configured for only allowing drug to pass into the suction part 503 of the pacifier 501*h'* when the user of the pacifier inhales, i.e. it can be configured to rotate into an open position when affected by an air flow from the user's inhaling and then get back to a closed state by for example a spring force when the user stops inhaling, i.e. there is no inhaling air flow from the user. Hereby it can be assured that drug is only delivered to the user during inhalation.

Figures 11A, 11B, 11C:
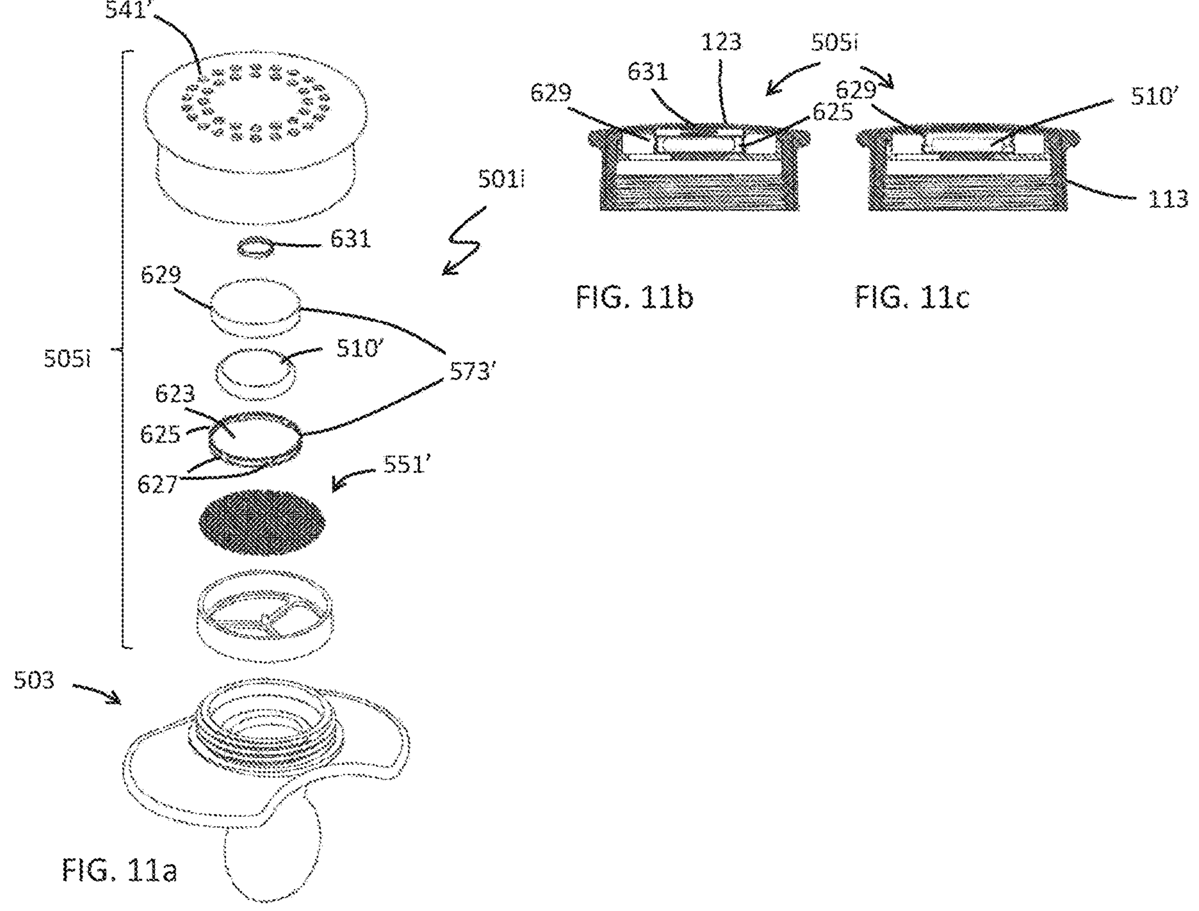
FIG. 11*a* is an exploded view in perspective of a pacifier according to another embodiment of the invention.
FIGS. 11*b* and 11*c* are cross sections of a housing part of the pacifier as shown in FIG. 11*a* in two different positions.
Figures 12A, 12B:
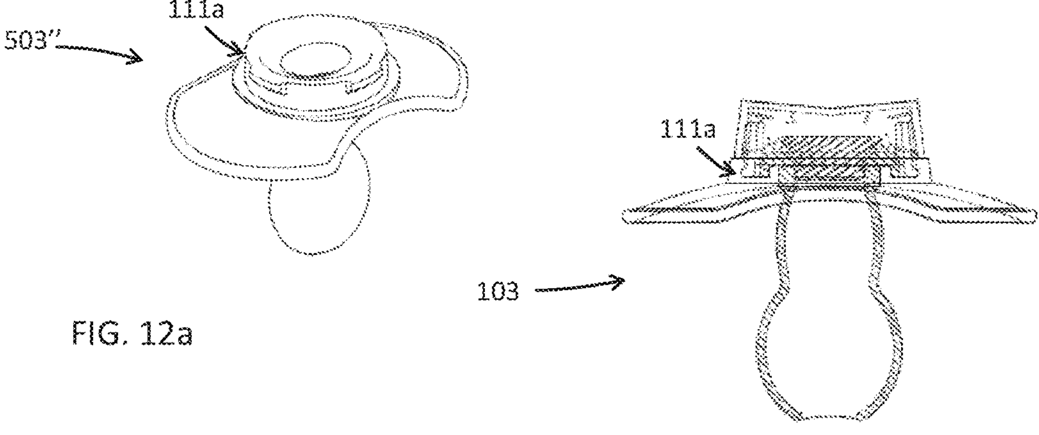
FIG. 12*a* is a perspective view of a suction part of a pacifier according to one embodiment of the invention comprising a different type of connection device.
FIG. 12*b* is a cross section of a suction part and a housing part according to another embodiment of the invention comprising still a different type of connection device.

In FIGS. 11*a*-11*c* still another embodiment of the invention is shown. In this embodiment the housing 113 further comprises a drug compartment 573' comprising a bottom 623 with attached side walls 625, wherein said side walls 625 comprises openings 627 through which the drug 510; 510', which is held in said drug compartment 573' can be released, whereby said drug compartment further comprises a movable cover 629 which can move into at least two positions whereby in a first position said movable cover 229 covers said openings 627 such that the drug is kept inside the drug compartment 573' and in a second position said movable cover 229 does not cover said openings 627 such that the drug can escape through said openings 627. The movable cover 629 is forced into said first position by a connected resilient device 631, for example a spring, and an air flow through the pacifier during inhalation by a user of the pacifier will force the movable cover 629 into said second position. Thanks to the venturi effect the pressure above the movable cover 629 will be lower during inhalation and therefore the movable cover will move towards the lid 123.

In any of the pacifier examples as described above in relation to FIGS. 1-11 a filter and/or a HME device could also be provided, in combination with the drug. In for example FIG. 4*e* a filter and/or HME device can easily be placed just below the lid to condition the air before reaching the one or more aerosolization membranes. And in FIGS. 1 and 2 a filter and/or a HME device can easily be provided within the housing 113 in addition to the drug 510 and the drug preparation device 551. The HME device and filter are further described below in relation to FIGS. 13-16.

According to another aspect of the to the invention an exchangeable housing part 505*a-i* configured to be used in a pacifier as described above is provided. The housing part 505*a*-505*i* comprises a housing 113 and at least one second connection device 111*b* which is releasably connectable to at least one first connection device 111*a* provided in the suction part 503; 503'; 503"; 103, wherein said housing 113 is prefilled with a drug which can pass through the passageway 117 into the mouth of the user when the housing part 505*a*-505*g* is connected to said suction part 503; 503'; 503"; 103 and wherein said drug is a drug to be inhaled through the passageway 117 of the suction part 503; 503'; 503"; 103. All the details described above with reference to the FIGS. 1-12 are also applicable to the exchangeable housing part 505*a-i* according to the invention and will not be described again.

FIGS. 13, 14 and 15 show schematically pacifiers comprising at least one of a HME device and/or a filter device which are very similar. Details which are the same are given the same reference numbers.

Figures 13A, 13B:
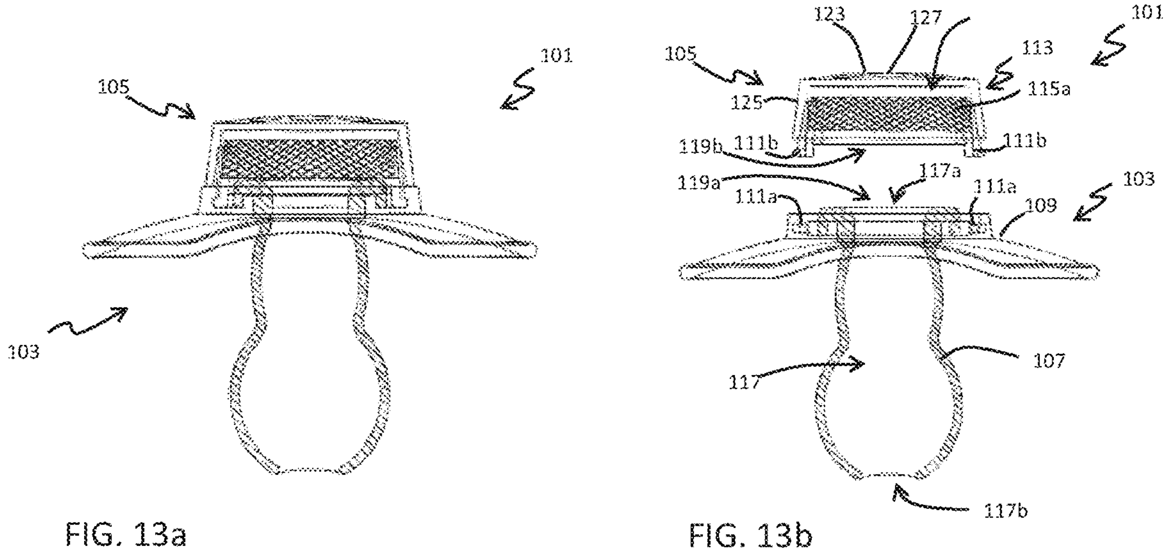
FIG. 13*a* shows schematically in cross section a pacifier comprising a HME device in an assembled position.
FIG. 13*b* shows the same pacifier as in FIG. 13*a* but in a separated position.

In FIGS. 13*a* and 13*b* a pacifier 101 comprising a HME device 115*a* is shown in assembled (FIG. 13*a*) and separated (FIG. 13*b*) positions. In FIGS. 14*a* and 14*b* a pacifier 101' comprising a filter device 115*b* is shown in assembled (FIG. 14*a*) and separated (FIG. 14*b*) positions. In FIG. 15 a pacifier 101" comprising both a HME device 115*a* and a filter device 115*b* is shown in separated position. FIG. 16*a* shows a pacifier in exploded view.

This could be any of the embodiments as shown in FIGS. 13-15. No filter device or HME device is shown in FIG. 16*a*. All these embodiments will now be described together referring to FIGS. 13-16.

A pacifier 101; 101'; 101" is provided which comprises a reusable suction part 103 and at least one exchangeable housing part 105 which are releasably connectable to each other. A pacifier system can also be provided comprising one suction part 103 and more than one housing parts 105 which are intended for use with the same suction part 103. Hereby the suction part 103 can be reused together with different housing parts 105. The housing parts 105 can be changed due to a need for changing or cleaning of the HME device 115*a* or filter device 115*b* provided therein or because there is a need for another type of HME device 115*a* or filter device 115*b*. Hereby the pacifier 101; 101'; 101" can be delivered as a kit with one suction part 103 and a number of housing parts 105. As a first option it is intended that the housing part is completely exchanged, i.e. the housing part is a single use part which is disposed after use. However, alternatively, instead of changing the whole housing part, the housing part can be released from the suction part and the filter device and/or HME device can be changed to a new one or cleaned for reuse.

The suction part 103 comprises a nipple 107 and a shield 109 connected to each other. The nipple 107 is configured to be sucked by a child and the shield 109 is provided for preventing swallowing of the nipple 107 as is common for pacifiers. According to the invention the suction part 103 comprises a passageway 117 through which a fluid can pass from outside a mouth of a user of the pacifier 101; 101'; 101" to inside the mouth of the user of the pacifier. Hereby the pacifier 101; 101'; 101" is a breath-through pacifier which is suitable to use for example when nose breathing is inhibited.

The suction part 103 comprises furthermore at least one first connection device 111*a* for connection with the housing part 105. The housing part 105 comprises a housing 113 and at least one second connection device 111*b* which is releasably connectable to the at least one first connection device 111*a*. In this embodiment the first connection device 111*a* comprises two opposing recesses and the second connection device 111*b* comprises two protruding parts, whereby the recesses are configured to receive the protruding parts when the suction part 103 and the housing part 105 are connected. For allowing the protruding parts to enter the recesses the protruding parts may be resilient. Another alternative is that for example the shield 109 is resilient and can be bent to allow the protruding parts to enter into the recesses. A still further alternative is shown in relation to FIG. 16*b* and will be further described below. In the embodiment described in relation to FIG. 16*b* the protruding parts do not need to be resilient. The number of recesses and protruding parts can of course be another than two. Furthermore, the recesses could as well be provided in the housing part 105 and the protruding parts in the suction part 103. For improving the connection and securing the connection a rotational locking feature can as well be provided. By rotating the housing part 105 in relation to the suction part 103 when they have been connected the first and second connection devices 111*a*, 111*b* can be provided in a locking position. For example the recesses can be provided as grooves allowing protruding parts to be guided in the grooves when the housing part is rotated.

An alternative connection and locking mechanism which can be used for connecting a suction part 103' (nipple not shown in this view) and a housing part 105' of a pacifier according to the invention is shown in FIG. 16*b*. In this embodiment of the locking mechanism a first connection device 111*a* provided in the suction part 103' comprises two protruding parts (however, the number of protruding parts can of course be varied). A second connection device 111*b* is provided in the housing part 105' and comprises two recesses 22' for receiving the protruding parts and a channel 23' into which the protruding parts 111*a* can be rotated, i.e. the recesses and channels allows rotation of the housing part in relation to the suction part when the protruding parts have been received in the recesses. A locking edge 22*a*' locks the protruding parts 111*a* within the channels 23'. The dimensions of the protruding parts 111*a*, the recesses 22' and the channels 23' can be provided such that friction between the parts keeps them connected to a requested strength but allows disengaging of the two parts. Furthermore, an inward angle of the channel 23' in relation to the recess 22' or an additional channel directed inwards can be adopted such that the housing part 105' needs to be pushed towards the somewhat inertially recoiling suction part 103' for allowing the rotation of the protruding parts 111*b* in the channels 23'. The channel thus forms more of a "U"-shape, with the tips of the U directed towards the suction part 103'.

Said housing 113 comprises at least one heat and moisture exchanger (HME) device 115*a* and/or at least one filter device 115_b_. In the embodiment as shown in FIGS. 13_a_ and 13_b_ the housing 113 comprises only a HME device 115_a_. In the embodiment as shown in FIGS. 14_a_ and 14_b_ the housing 113 comprises only a filter device 115_b_ and in the embodiment as shown in FIG. 15 the housing 113 comprises both a HME device 115_a_ and a filter device 115_b_.

The passageway 117 comprises a first end 117_a_ and a second end 117_b_ between which a fluid can pass, which first end 117_a_ is provided at a first connection interface 119_a_ of the suction part 103 which is configured for mating with a second connection interface 119_b_ of the housing part 105. The second end 117_b_ of the passageway 117 is provided in a part of the nipple 107 which is configured to be positioned within a user's mouth during use of the pacifier 101; 101'; 101", whereby a fluid can pass through the passageway 117 between the first connection interface 119_a_ of the suction part 103 and the inside of a user's mouth during use of the pacifier. The passageway 117 is hereby extending through the nipple 107 and through the shield 109.

The housing 113 of the housing part 105 comprises an interior space 121 which is defined by a lid 123, surrounding walls 125 connected to the lid 123 and the second connection interface 119_b_ which is provided opposite the lid 123. Said second connection interface 119_b_ is at least partly open into the interior space 121 of the housing 113 and is configured for mating with the first connection interface 119_a_ of the suction part 103.

Furthermore, the lid 123 comprises air openings 127 through which air can pass. The HME device 115_a_ and/or the filter device 115_b_ are provided within the interior space 121 of the housing 113 such that air passing between the air openings 127 in the lid 123 and the second connection surface 119_b_ of the housing 113 also has to pass the HME device 115_a_ and/or the filter device 115_b_.

In some embodiments the HME device 115_a_ and/or the filter device 115_b_ can be secured within the interior space 121 of the housing 113 by at least one grating 131 which is welded to the surrounding walls 125. Such a grating is shown in FIG. 16_a_.

According to the invention a pacifier system is also provided. This is illustrated in FIG. 17. A pacifier system according to the invention comprises a reusable suction part 503; 503'; 503"; 103 and at least two exchangeable housing parts 505_a-i_; 105; 305. The exchangeable housing parts 505_a-i_; 105; 305 can comprise a drug to be inhaled as described in relation to FIGS. 1-11, a drug to be swallowed (enteral drug), a heat and moisture exchanger (HME) device or a filter or more than one of these different examples in combination. For example, an exchangeable housing part may comprise both a drug and a filter. By providing a pacifier system one suction part can be used for different types of housing parts and a suitable housing part can be provided for different occasions. Furthermore, new housing parts can be provided when the first one is empty of drug or when a filter needs to be changed. Hereby a user friendly and environmentally friendly product which is flexible for different needs is achieved.

The invention claimed is:

1. A pacifier comprising a suction part and a housing part,
wherein said suction part comprises a nipple and a shield connected to each other,
wherein said suction part comprises a passageway through which a fluid can pass from outside a mouth of a user of the pacifier to inside the mouth of the user of the pacifier,
and wherein said housing part comprises a housing, wherein said housing is prefilled with a drug which can pass through the passageway into the mouth of the user when the housing part is connected to said suction part and wherein said drug is a drug to be inhaled through the passageway of the suction part, and
wherein said housing part comprises a drug preparation device configured for transferring the drug to the suction part in a form for inhalation,
wherein said housing comprises at least one air inlet, whereby air can be drawn into the housing through said at least one air inlet by the user of the pacifier when the user is inhaling through the passageway of the suction part,
wherein the suction part is a reusable part and the housing part is an exchangeable part, wherein said reusable suction part and said exchangeable housing part are releasable connectable to each other, wherein said suction part comprises at least one first connection device and wherein said housing part comprises at least one second connection device which is releasably connectable to the at least one first connection device.

2. Pacifier according to claim 1, wherein the at least one air inlet is provided with at least one valve such that passage of air via said at least one air inlet only is admitted into and not out from said housing.

3. Pacifier according to claim 1, wherein said drug is a powder drug for inhalation and wherein said drug preparation device comprises a turbulence device and a dosing device.

4. Pacifier according to claim 1, wherein said drug is a liquid drug for inhalation and wherein said drug preparation device comprises an aerosolization device.

5. Pacifier according to claim 4, wherein said aerosolization device comprises at least one aerosolization membrane which is a fine pore membrane and/or an oscillating membrane, whereby said liquid drug will be aerosolized when forced through said at least one aerosolization membrane.

6. Pacifier according to claim 4, wherein said aerosolization device comprises an oscillating membrane, wherein said oscillating membrane is configured for starting to oscillate when the user of the pacifier inhales whereby the liquid drug will be aerosolized by said oscillations and whereby said oscillating membrane comprises pores which are of a size such that aerosolized drug can pass through the oscillating membrane and further through the housing part to a fine pore membrane or to the passageway of the suction part.

7. Pacifier according to claim 1, wherein said housing part further comprises a piercing member arranged for piercing a drug capsule in which said drug is provided when said housing part is provided in a certain position in relation to the suction part hereby allowing the drug to be released from the drug capsule at a certain moment.

8. Pacifier according to claim 7, wherein said drug is provided in more than one drug capsule and wherein said housing part can be provided in more than one different positions in relation to the suction part whereby said piercing member will be piercing one drug capsule in each of said positions.

9. Pacifier according to claim 1, wherein the drug is provided inside a capsule having a breakable capsule cover whereby the capsule has a size such that the capsule will be compressed and broken when the suction part and the housing part are connected.

10. Pacifier according to claim 1, wherein a lid of the housing comprises at least one air inlet through which air can pass and wherein the drug is provided within an interior space of the housing such that air passing between the at least one air inlet in the lid and a second connection surface of the housing which is provided opposite the lid also passes the drug.

11. Pacifier according to claim 1, wherein at least one separate air channel is provided in the housing part, wherein said at least one separate air channel is provided in fluid connection to at least one open air inlet of the housing part which is not in communication with a drug compartment of the housing where the drug initially is provided and wherein said at least one open air inlet is open for passage of air in both directions.

12. Pacifier according to claim 1, wherein said housing of said housing part comprises a pressurized chamber and/or a biased resilient member which can be activated for providing a pressure to the drug for transferring the drug to the passageway of the suction part.

13. Pacifier according to claim 12, wherein said pressurized chamber comprises a releasing device, whereby said releasing device can be moved by an air flow provided through the pacifier during inhalation by the user, whereby said pressurized chamber is activated by a movement of said releasing device for providing a pressure to the drug for transferring the drug to the passageway of the suction part.

14. Pacifier according to claim 1, wherein said housing further comprises a drug compartment comprising a bottom with attached side walls, wherein said side walls comprises openings through which the drug which is held in said drug compartment can be released, whereby said drug compartment further comprises a movable cover which can move into at least two positions whereby in a first position said movable cover covers said openings such that the drug is kept inside the drug compartment and in a second position said movable cover does not cover said openings such that the drug can escape through said openings, whereby said movable cover is forced into said first position by a connected resilient device and whereby an air flow through the pacifier during inhalation by the user of the pacifier will force the movable cover into said second position.

15. A pacifier comprising a suction part and a housing part, wherein said suction part comprises a nipple and a shield connected to each other wherein said suction part comprises a passageway through which a fluid can pass from outside a mouth of a user of the pacifier to inside the mouth of the user of the pacifier, and wherein said housing part comprises a housing, wherein said housing is prefilled with a drug which can pass through the passageway into the mouth of the user when the housing part is connected to said suction part and wherein said drug is a drug to be inhaled through the passageway of the suction part, and wherein said housing part comprises a drug preparation device configured for transferring the drug to the suction part in a form for inhalation wherein said passageway comprises a first end and a second end between which a fluid can pass, which the first end is provided at a first connection interface of the suction part configured for mating with a second connection interface of the housing part and which the second end of the passageway is provided in a part of the nipple which is configured to be positioned within the user's mouth during use of the pacifier, whereby a fluid can pass through the passageway between the first connection interface of the suction part and the inside of the user's mouth during use of the pacifier; and wherein the housing of the housing part comprises an interior space which is defined by a lid, surrounding walls and the second connection interface which is provided opposite the lid, wherein said second connection interface is configured for mating with the first connection interface of the suction part.

16. Pacifier according to claim 15, wherein the housing part or the suction part comprises at least one protruding part which will push the second connection interface towards the lid when the housing part and the suction part are connected whereby a pressure will be provided to the interior space, in which the drug initially is provided.

17. An exchangeable housing part configured to be used with the suction part according to claim 1, wherein said housing part comprises a housing and at least one second connection device which is releasably connectable to at least one first connection device provided in the suction part, wherein said housing is prefilled with a drug which can pass through the passageway into the mouth of the user when the housing part is connected to said suction part and wherein said drug is a drug to be inhaled through the passageway of the suction part, wherein said housing part comprises a drug preparation device configured for transferring the drug to the suction part in a form for inhalation, wherein said housing comprises at least one air inlet, whereby air can be drawn into the housing through said at least one air inlet by the user of the pacifier when the user is inhaling through the passageway of the suction part, and wherein the at least one air inlet is provided with at least one valve such that passage of air via said at least one air inlet only is admitted into and not out from said housing.

18. A pacifier system comprising a pacifier comprising a suction part and a housing part, wherein said suction part comprises a nipple and a shield connected to each other, wherein said suction part comprises a passageway through which a fluid can pass from outside a mouth of a user of the pacifier to inside the mouth of the user of the pacifier, and wherein said housing part comprises a housing, wherein said housing is prefilled with a drug which can pass through the passageway into the mouth of the user when the housing part is connected to said suction part and wherein said drug is a drug to be inhaled through the passageway of the suction part, and wherein said housing part comprises a drug preparation device configured for transferring the drug to the suction part in a form for inhalation, wherein the housing part is an exchangeable housing part and wherein the pacifier system comprises at least one of another of the exchangeable housing parts or a second exchangeable housing part comprising at least one heat and moisture exchanger (HME) device and/or at least one filter device.

* * * * *